(12) United States Patent
Alejandro et al.

(10) Patent No.: US 7,972,330 B2
(45) Date of Patent: *Jul. 5, 2011

(54) METHODS AND APPARATUS FOR CLOSING A LAYERED TISSUE DEFECT

(75) Inventors: Jose Alejandro, Sunnyvale, CA (US); Mark E. Deem, Mountain View, CA (US); Erik Engelson, Menlo Park, CA (US); Dominique Filloux, Redwood City, CA (US); Dan Francis, Mountain View, CA (US); Hanson Gifford, Woodside, CA (US); Kenneth Horne, San Francisco, CA (US); Uday N. Kumar, San Francisco, CA (US); William Malecki, San Francisco, CA (US); Miriam H. Taimisto, San Jose, CA (US); Venkata Vegesna, Sunnyvale, CA (US)

(73) Assignee: Terumo Kabushiki Kaisha, Tokyo (JP)

( * ) Notice: Subject to any disclaimer, the term of this patent is extended or adjusted under 35 U.S.C. 154(b) by 1166 days.

This patent is subject to a terminal disclaimer.

(21) Appl. No.: 11/613,415

(22) Filed: Dec. 20, 2006

(65) Prior Publication Data

US 2007/0123851 A1 May 31, 2007

Related U.S. Application Data

(60) Continuation-in-part of application No. 10/958,533, filed on Oct. 4, 2004, which is a division of application No. 10/679,245, filed on Oct. 2, 2003, now Pat. No. 6,939,348.

(60) Provisional application No. 60/458,854, filed on Mar. 27, 2003, provisional application No. 60/478,035, filed on Jun. 11, 2003, provisional application No. 60/490,082, filed on Jul. 24, 2003.

(51) Int. Cl.
*A61B 18/14* (2006.01)

(52) U.S. Cl. .......................... 606/41; 606/216

(58) Field of Classification Search .............. 606/27–31, 606/41, 47–50, 213–216; 128/898
See application file for complete search history.

(56) References Cited

U.S. PATENT DOCUMENTS 2,275,167 A 3/1942 Bierman
(Continued)

FOREIGN PATENT DOCUMENTS

EP 135840 A2 4/1985
(Continued)

OTHER PUBLICATIONS

Anzola et al., "Potential Source of Cerebral Embolism in Migraine with Aura," *Neurology* (1999) 52(8): 1622.
(Continued)

*Primary Examiner* — Michael Peffley
(74) *Attorney, Agent, or Firm* — Oblon, Spivak, McClelland, Maier & Neustadt, L.L.P.

(57) ABSTRACT

Methods and apparatus for treatment of layered tissue defects such as a patent foramen ovale provide for applying energy to tissues adjacent to the PFO with a closure device that substantially closes the PFO. Apparatus generally includes an elongate flexible member having a proximal end and a distal end and an energy transmission member deployable from the elongate flexible member. The energy transmission member applies energy to the layered tissue defect at a first position and a second position adjacent to the first position so as to substantially close the layered tissue defect along at least a portion of the defect. Applied energy may be monopolar or bipolar radiofrequency energy or any other suitable energy, such as laser, microwave, ultrasound, resistive heating, direct heat energy, cryogenic or the like. PFO closure via energy-based approaches of the invention may help prevent stroke, treat migraine headache, and possibly treat or prevent other medical conditions.

21 Claims, 29 Drawing Sheets

U.S. PATENT DOCUMENTS

| | | | |
|---|---|---|---|
| 2,580,628 A | 1/1952 | Welsh | |
| 2,888,928 A | 6/1959 | Seiger | |
| 3,490,442 A | 1/1970 | Streu | |
| 3,862,627 A | 1/1975 | Hans, Sr. | |
| 3,874,388 A | 4/1975 | King et al. | |
| 3,906,955 A | 9/1975 | Roberts | |
| 4,307,720 A | 12/1981 | Weber, Jr. | |
| 4,326,529 A | 4/1982 | Doss et al. | |
| 4,473,077 A | 9/1984 | Noiles et al. | |
| 4,485,817 A | 12/1984 | Swiggett | |
| 4,532,924 A | 8/1985 | Auth et al. | |
| 4,556,065 A | 12/1985 | Hoffmann | |
| 4,562,838 A | 1/1986 | Walker | |
| 4,590,934 A | 5/1986 | Malis et al. | |
| 4,682,596 A | 7/1987 | Bales et al. | |
| 4,788,975 A | 12/1988 | Shturman et al. | |
| 4,798,594 A | 1/1989 | Hillstead | |
| 4,832,048 A | 5/1989 | Cohen | |
| 4,884,567 A | 12/1989 | Elliott et al. | |
| 4,895,565 A | 1/1990 | Hillstead | |
| 4,911,159 A | 3/1990 | Johnson et al. | |
| 4,919,129 A | 4/1990 | Weber, Jr. et al. | |
| 4,929,246 A | 5/1990 | Sinofsky | |
| 4,976,711 A | 12/1990 | Parins et al. | |
| 4,986,889 A | 1/1991 | Charamathieu et al. | |
| 5,041,095 A | 8/1991 | Littrell | |
| 5,042,707 A | 8/1991 | Taheri | |
| 5,055,100 A | 10/1991 | Olsen | |
| 5,056,517 A | 10/1991 | Fenici | |
| 5,057,107 A | 10/1991 | Parins et al. | |
| 5,071,417 A | 12/1991 | Sinofsky | |
| 5,071,418 A | 12/1991 | Rosenbaum | |
| 5,078,717 A | 1/1992 | Parins et al. | |
| 5,099,827 A | 3/1992 | Melzer et al. | |
| RE33,925 E | 5/1992 | Bales et al. | |
| 5,125,928 A | 6/1992 | Parins et al. | |
| 5,156,608 A | 10/1992 | Troidl et al. | |
| 5,156,613 A | 10/1992 | Sawyer | |
| 5,171,311 A | 12/1992 | Rydell | |
| 5,195,959 A | 3/1993 | Smith | |
| 5,196,007 A | 3/1993 | Ellman et al. | |
| 5,197,963 A | 3/1993 | Parins | |
| 5,207,670 A | 5/1993 | Sinofsky | |
| 5,209,756 A | 5/1993 | Seedhom et al. | |
| 5,290,278 A | 3/1994 | Anderson | |
| 5,292,362 A | 3/1994 | Bass et al. | |
| 5,295,955 A | 3/1994 | Rosen et al. | |
| 5,300,065 A | 4/1994 | Anderson | |
| 5,336,221 A | 8/1994 | Anderson | |
| 5,336,252 A | 8/1994 | Cohen | |
| 5,342,413 A | 8/1994 | Hirschberg et al. | |
| 5,345,935 A | 9/1994 | Hirsch | |
| 5,370,675 A | 12/1994 | Edwards et al. | |
| 5,380,304 A | 1/1995 | Parker | |
| 5,383,917 A | 1/1995 | Desai et al. | |
| 5,405,322 A | 4/1995 | Lennox et al. | |
| 5,409,479 A | 4/1995 | Dew et al. | |
| 5,409,481 A | 4/1995 | Poppas et al. | |
| 5,500,012 A | 3/1996 | Brucker et al. | |
| 5,505,730 A | 4/1996 | Edwards | |
| 5,507,744 A | 4/1996 | Tay et al. | |
| 5,540,677 A | 7/1996 | Sinofsky | |
| 5,569,239 A | 10/1996 | Sinofsky | |
| 5,571,216 A | 11/1996 | Anderson | |
| 5,575,772 A | 11/1996 | Lennox | |
| 5,584,872 A | 12/1996 | Lafontaine et al. | |
| 5,611,794 A | 3/1997 | Sauer et al. | |
| 5,620,481 A | 4/1997 | Desai et al. | |
| 5,626,607 A | 5/1997 | Malecki et al. | |
| 5,662,643 A | 9/1997 | Kung et al. | |
| 5,665,109 A | 9/1997 | Yoon | |
| 5,669,934 A | 9/1997 | Sawyer | |
| 5,693,078 A | 12/1997 | Desai et al. | |
| 5,709,224 A * | 1/1998 | Behl et al. | 128/898 |
| 5,713,891 A | 2/1998 | Poppas | |
| 5,725,522 A | 3/1998 | Sinofsky | |
| 5,730,742 A | 3/1998 | Wojciechowicz | |
| 5,749,895 A | 5/1998 | Sawyer et al. | |
| 5,782,899 A | 7/1998 | Imran | |
| 5,814,065 A | 9/1998 | Diaz | |
| 5,824,015 A | 10/1998 | Sawyer | |
| 5,827,265 A | 10/1998 | Glinsky et al. | |
| 5,827,268 A | 10/1998 | Laufer | |
| 5,846,196 A | 12/1998 | Siekmeyer et al. | |
| 5,855,312 A | 1/1999 | Toledano | |
| 5,871,443 A | 2/1999 | Edwards et al. | |
| 5,919,200 A | 7/1999 | Stambaugh et al. | |
| 5,925,078 A | 7/1999 | Anderson | |
| 5,928,266 A | 7/1999 | Kontos | |
| 5,931,165 A | 8/1999 | Reich et al. | |
| 5,944,738 A | 8/1999 | Amplatz et al. | |
| 5,972,023 A | 10/1999 | Tanner et al. | |
| 5,972,024 A | 10/1999 | Northrup, III et al. | |
| 6,004,316 A | 12/1999 | Laufer | |
| 6,012,457 A | 1/2000 | Lesh | |
| 6,036,699 A | 3/2000 | Andreas et al. | |
| 6,050,994 A | 4/2000 | Sherman | |
| 6,056,760 A | 5/2000 | Koike et al. | |
| 6,063,081 A | 5/2000 | Mulier | |
| 6,063,085 A * | 5/2000 | Tay et al. | 606/50 |
| 6,083,223 A | 7/2000 | Baker | |
| 6,086,570 A | 7/2000 | Aboul-Hosn et al. | |
| 6,086,586 A | 7/2000 | Hooven | |
| 6,087,552 A | 7/2000 | Gregory | |
| 6,092,528 A | 7/2000 | Edwards | |
| 6,132,429 A | 10/2000 | Baker | |
| 6,149,660 A | 11/2000 | Laufer et al. | |
| 6,156,032 A | 12/2000 | Lennox | |
| 6,168,594 B1 | 1/2001 | Lafontaine | |
| 6,211,335 B1 | 4/2001 | Owen et al. | |
| 6,221,068 B1 | 4/2001 | Fried et al. | |
| 6,236,875 B1 | 5/2001 | Bucholz | |
| 6,248,124 B1 | 6/2001 | Pedros et al. | |
| 6,257,241 B1 | 7/2001 | Wampler | |
| 6,290,674 B1 | 9/2001 | Roue et al. | |
| 6,302,898 B1 | 10/2001 | Edwards et al. | |
| 6,323,037 B1 | 11/2001 | Lauto et al. | |
| 6,325,798 B1 | 12/2001 | Edwards et al. | |
| 6,355,030 B1 | 3/2002 | Aldrich et al. | |
| 6,358,246 B1 | 3/2002 | Behl et al. | |
| 6,375,668 B1 | 4/2002 | Gifford et al. | |
| 6,383,198 B1 | 5/2002 | Hamilton | |
| 6,391,048 B1 | 5/2002 | Ginn et al. | |
| 6,391,049 B1 | 5/2002 | McNally et al. | |
| 6,398,779 B1 | 6/2002 | Buysse et al. | |
| 6,398,782 B1 | 6/2002 | Pecor et al. | |
| 6,398,797 B2 | 6/2002 | Bombard et al. | |
| 6,401,720 B1 | 6/2002 | Stevens et al. | |
| 6,409,720 B1 | 6/2002 | Hissong et al. | |
| 6,413,254 B1 | 7/2002 | Hissong et al. | |
| 6,419,669 B1 | 7/2002 | Frazier et al. | |
| 6,423,057 B1 | 7/2002 | He et al. | |
| 6,436,088 B2 | 8/2002 | Frazier et al. | |
| 6,451,013 B1 | 9/2002 | Bays et al. | |
| 6,456,865 B2 | 9/2002 | Samson | |
| 6,458,100 B2 | 10/2002 | Roue et al. | |
| 6,475,213 B1 | 11/2002 | Whayne et al. | |
| 6,482,224 B1 | 11/2002 | Michler et al. | |
| 6,514,250 B1 | 2/2003 | Jahns et al. | |
| 6,558,314 B1 | 5/2003 | Adelman et al. | |
| 6,558,382 B2 | 5/2003 | Jahns et al. | |
| 6,562,037 B2 | 5/2003 | Paton et al. | |
| 6,583,117 B2 | 6/2003 | Owen et al. | |
| 6,584,360 B2 | 6/2003 | Francischelli et al. | |
| 6,589,237 B2 | 7/2003 | Woloszko | |
| 6,606,523 B1 | 8/2003 | Jenkins | |
| 6,641,604 B1 | 11/2003 | Adelman | |
| 6,645,202 B1 | 11/2003 | Pless et al. | |
| 6,645,225 B1 | 11/2003 | Atkinson | |
| 6,648,897 B2 | 11/2003 | Hamilton | |
| 6,652,518 B2 | 11/2003 | Wellman | |
| 6,669,693 B2 | 12/2003 | Friedman | |
| 6,676,685 B2 | 1/2004 | Pedros et al. | |
| 6,682,546 B2 | 1/2004 | Amplatz | |
| 6,692,450 B1 | 2/2004 | Coleman | |
| 6,702,835 B2 | 3/2004 | Ginn | |
| 6,712,804 B2 | 3/2004 | Roue et al. | |

| | | |
|---|---|---|
| 6,712,836 B1 | 3/2004 | Berg et al. |
| 6,716,211 B2 | 4/2004 | Mulier et al. |
| 6,726,718 B1 | 4/2004 | Carlyle et al. |
| 6,730,108 B2 | 5/2004 | Van Tassel et al. |
| 6,733,498 B2 | 5/2004 | Paton et al. |
| 6,736,810 B2 | 5/2004 | Hoey et al. |
| 6,755,790 B2 | 6/2004 | Stewart et al. |
| 6,770,072 B1 | 8/2004 | Truckai et al. |
| 6,776,784 B2 | 8/2004 | Ginn |
| 6,790,218 B2 | 9/2004 | Jayaraman |
| 6,846,319 B2 | 1/2005 | Ginn et al. |
| 6,887,238 B2 | 5/2005 | Jahns |
| 6,893,431 B2 | 5/2005 | Naimark et al. |
| 6,893,442 B2 | 5/2005 | Whayne |
| 6,918,908 B2 | 7/2005 | Bonner et al. |
| 6,926,716 B2 | 8/2005 | Baker et al. |
| 6,929,644 B2 | 8/2005 | Truckai et al. |
| 6,932,812 B2 | 8/2005 | Crowley et al. |
| 6,939,348 B2 | 9/2005 | Malecki et al. |
| 6,946,134 B1 | 9/2005 | Rosen et al. |
| 6,960,205 B2 | 11/2005 | Jahns et al. |
| 7,025,756 B2 | 4/2006 | Frazier et al. |
| 7,094,215 B2 | 8/2006 | Davison et al. |
| 7,165,552 B2 | 1/2007 | Deem et al. |
| 7,238,182 B2 | 7/2007 | Swoyer et al. |
| 7,637,924 B2 * | 12/2009 | Gifford et al. ................. 606/213 |
| 7,678,133 B2 * | 3/2010 | Modesitt ....................... 606/216 |
| 2001/0020166 A1 | 9/2001 | Daly et al. |
| 2001/0037129 A1 | 11/2001 | Thill |
| 2001/0051803 A1 | 12/2001 | Desai et al. |
| 2002/0128672 A1 | 9/2002 | Dinger et al. |
| 2002/0143322 A1 | 10/2002 | Haghighi |
| 2002/0156472 A1 | 10/2002 | Lee et al. |
| 2003/0028189 A1 | 2/2003 | Woloszko et al. |
| 2003/0045893 A1 | 3/2003 | Ginn |
| 2003/0050665 A1 | 3/2003 | Ginn |
| 2003/0065364 A1 | 4/2003 | Wellman et al. |
| 2003/0069570 A1 | 4/2003 | Witzel |
| 2003/0078578 A1 | 4/2003 | Truckai et al. |
| 2003/0092988 A1 | 5/2003 | Makin |
| 2003/0093071 A1 | 5/2003 | Hauck et al. |
| 2003/0120268 A1 | 6/2003 | Bertolero et al. |
| 2003/0144652 A1 | 7/2003 | Baker et al. |
| 2003/0144694 A1 | 7/2003 | Chanduszko et al. |
| 2003/0158551 A1 | 8/2003 | Paton et al. |
| 2003/0199868 A1 | 10/2003 | Desai et al. |
| 2003/0208232 A1 | 11/2003 | Blaeser |
| 2003/0225421 A1 | 12/2003 | Peavey et al. |
| 2003/0233091 A1 | 12/2003 | Whayne et al. |
| 2004/0059347 A1 | 3/2004 | Hamilton |
| 2004/0092973 A1 | 5/2004 | Chanduszko et al. |
| 2004/0098031 A1 | 5/2004 | van der Burg et al. |
| 2004/0098042 A1 | 5/2004 | Devellian et al. |
| 2004/0102721 A1 | 5/2004 | McKinley |
| 2004/0143292 A1 | 7/2004 | Marino et al. |
| 2004/0153057 A1 | 8/2004 | Davison |
| 2004/0153098 A1 | 8/2004 | Chin et al. |
| 2004/0176799 A1 | 9/2004 | Chanduszko et al. |
| 2004/0220596 A1 | 11/2004 | Frazier et al. |
| 2004/0243122 A1 * | 12/2004 | Auth et al. ....................... 606/41 |
| 2004/0249398 A1 | 12/2004 | Ginn |
| 2005/0021059 A1 | 1/2005 | Cole et al. |
| 2005/0033288 A1 | 2/2005 | Auth et al. |
| 2005/0033327 A1 | 2/2005 | Gainor et al. |
| 2005/0055050 A1 | 3/2005 | Alfaro |
| 2005/0065506 A1 | 3/2005 | Phan |
| 2005/0065509 A1 | 3/2005 | Coldwell et al. |
| 2005/0070923 A1 | 3/2005 | Mcintosh |
| 2005/0075665 A1 | 4/2005 | Brenzel et al. |
| 2005/0119675 A1 | 6/2005 | Adams et al. |
| 2005/0125032 A1 | 6/2005 | Whisenant et al. |
| 2005/0171526 A1 | 8/2005 | Rioux et al. |
| 2005/0187568 A1 | 8/2005 | Klenk et al. |
| 2005/0192626 A1 | 9/2005 | Widomski et al. |
| 2005/0192627 A1 | 9/2005 | Whisenant et al. |
| 2005/0192654 A1 | 9/2005 | Chanduszko et al. |
| 2005/0209636 A1 | 9/2005 | Widomski et al. |
| 2005/0216054 A1 | 9/2005 | Widomski et al. |
| 2005/0251201 A1 | 11/2005 | Roue et al. |
| 2005/0256532 A1 | 11/2005 | Nayak et al. |
| 2005/0267495 A1 | 12/2005 | Ginn et al. |
| 2005/0267525 A1 | 12/2005 | Chanduszko |
| 2006/0009762 A1 | 1/2006 | Whayne |
| 2006/0036284 A1 | 2/2006 | Blaeser et al. |
| 2006/0052821 A1 | 3/2006 | Abbott et al. |
| 2006/0069408 A1 | 3/2006 | Kato |
| 2006/0079870 A1 | 4/2006 | Barry |
| 2006/0079887 A1 | 4/2006 | Buysse et al. |
| 2006/0173510 A1 | 8/2006 | Besio et al. |
| 2007/0088355 A9 | 4/2007 | Auth |

FOREIGN PATENT DOCUMENTS

| | | |
|---|---|---|
| EP | 199694 A2 | 10/1986 |
| EP | 0265532 A1 | 5/1988 |
| EP | 0375556 A1 | 6/1990 |
| EP | 0428812 A1 | 5/1991 |
| EP | 0947165 A1 | 10/1999 |
| GB | 1260919 | 1/1972 |
| GB | 1550676 | 8/1979 |
| GB | 2 359 024 A | 8/2001 |
| WO | WO 85/00018 A1 | 1/1985 |
| WO | WO 87/04081 A1 | 7/1987 |
| WO | WO 90/04352 A1 | 5/1990 |
| WO | WO 91/15996 A1 | 10/1991 |
| WO | WO 92/04864 A1 | 4/1992 |
| WO | WO 93/05705 A1 | 4/1993 |
| WO | WO 93/15791 A1 | 8/1993 |
| WO | WO 94/00178 A1 | 1/1994 |
| WO | WO 98/07375 A1 | 2/1998 |
| WO | WO 99/18862 A1 | 4/1999 |
| WO | WO 99/18864 A1 | 4/1999 |
| WO | WO 99/18870 A1 | 4/1999 |
| WO | WO 99/18871 A1 | 4/1999 |
| WO | WO 99/23959 A1 | 5/1999 |
| WO | WO 99/49788 A | 10/1999 |
| WO | WO 00/07506 A2 | 2/2000 |
| WO | WO 00/09027 A1 | 2/2000 |
| WO | WO 01/13810 A1 | 3/2001 |
| WO | WO 01/78596 A1 | 10/2001 |
| WO | WO 01/82778 A | 11/2001 |
| WO | WO 03/022159 A1 | 3/2003 |
| WO | WO 03/022160 A1 | 3/2003 |
| WO | WO 03/026496 A2 | 4/2003 |
| WO | WO 03/053493 A2 | 7/2003 |
| WO | WO 03/071957 A2 | 9/2003 |
| WO | WO 03/082076 A2 | 10/2003 |
| WO | WO 03/094742 A1 | 11/2003 |
| WO | WO 2004/019791 A2 | 3/2004 |
| WO | WO 2004/043266 A2 | 5/2004 |
| WO | WO 2004/069055 A2 | 8/2004 |
| WO | WO 2004/082532 A1 | 9/2004 |
| WO | WO 2004/091411 A2 | 10/2004 |
| WO | WO 2005/006990 A2 | 1/2005 |
| WO | WO 2005/027753 A1 | 3/2005 |
| WO | WO 2005/034738 A2 | 4/2005 |
| WO | WO 2005/074814 A2 | 8/2005 |
| WO | WO 2005/046487 A1 | 12/2005 |
| WO | WO 2005/115256 A | 12/2005 |

OTHER PUBLICATIONS

Athiraman et al., "Selective Photothermal Tissue Interaction Using 805-nm Laser and Indocyanine Green in Tissue Welding," *Journal of X-Ray Science and Technology*, vol. 12, No. 2, (2004), pp. 117-126.

De Castro et al., "Morphological and Functional Characteristics of Patent Foramen Ovale and Their Embolic Implications," *Stroke* (Oct. 2002), pp. 2407-2413.

Cordis Corporation, Cordis Ducor® Lumeleo™ Electorode Catheters [brochure], Cordis Corporation, (Dec. 1984), 2 pages.

Del Sette, "Migrane with Aura and Right-to-Left Shunt on Transcranial Doppler: A Case Control Study," *Cerebrovas Dis* (1998) 8:327-330.

Fenner et al., "Shear Strength of Tissue Bonds as a Function of Bonding Temperature: A Proposed Mechanism for Laser-Assisted Tissue Welding," *Lasers in Medical Science*, vol. 7, (1992), pp. 39-43.

Godlewski et al., "Applications and Mechanisms of Laser Tissue Welding in 1995: Review," *Proc. SPIE*, vol. 2623, (Jan. 1996) pp. 334-341.

Gillette, "Catheter Ablation in Dysrhythmias," *Cardio*, (Mar. 1984), pp. 67-69.

Ho et al., "Morphological Features Pertinent to Interventional Closure of Patent Oval Foramen," *J Interventional Cardiology*, vol. 16 No. 1, (2003), pp. 33-34.

Kennedy et al., "High-burst-Strength, feedback-controlled bipolar vessel sealing," *Surg Endosc* (1998) 12:876-878.

Koenig et al., "Role of Intracardiac Echocardiographic Guidance in Transcatheter Closure of Atrial Septal Defects and Patent Foramen Ovale Using the Amplatzer® Device," *J. Interventional Cardiology*, (2003) 16 (1): 51-62.

Morady, "Transvenous Catheter Ablation of a Posterospetial Accessory Pathway in a Patient with the Wolff Parkinson-White Syndrome," *The New England Journal of Medicine*, (Mar. 15, 1984), 310(11): 705-707.

Morandi et al., "Transcatheter Closure of Patent Foramen Ovale: A New Migraine Treatment?" *J Interventional Cardiology*, (2003), 16(1): 39-42.

Olson et al., "Developing an Animal Model for the Study of Fusion Using RF Energy," *Proc. SPIE*, vol. 5312, (2004), pp. 147-161.

Ott et al., "Comparative in Vitro Study of Tissue Welding Using a 808 nm Diode Laser and a Ho:YAG laser," *Lasers Med Sci*, vol. 16, (2001) pp. 260-266.

Pfleger, "Haemodynamic Quantification of Different Provocation Manoeuvres by Simultaneous Measurement of Right and Left Atrial Pressure: Implications for the Echocardiographic Detection of Persistent Foramen Ovale," *Eur J Echocardiography* (2001) 2: 88-93.

Polgar et al., "A New Technique for Closed-Chest Human His Bundle Ablation Using Suction Electrode Catheter and DC Shock," In: Perez Gomez F, ed. Cardiac Pacing Electrophysiology Tachyarrhythmias. Madrid, Spain: Grouz Publishers; 1985:1582-1586.

Polgar et al., "Comparison of Two Different Techniques for Closed-Chest His Bundle Ablation," In: Perez Gomez F, ed. Cardiac Pacing Electrophysiology Tachyarrhythmias. Madrid, Spain: Grouz Publishers: 1985:1578-1587.

Polgar, "Closed Chested Ablation of His Bundle: A New Technique Using Suction Electorde Catheter and DC Shock," *Nachdruck Aus: Cardio Pacing*, (1983), pp. 883-890.

Poppas et al., "Temperature-Controlled Laser Photocoagulation of Soft Tissue: in Vivo Evaluation Using a Tissue Welding Model," Lasers Surg Med., vol. 18, No. 4, (1996), pp. 335-344.

Stewart et al., "Laser Assisted Vascular Welding with Real Time Temperature Control," Lasers Surg Med., vol. 19, No. 1, (1996), pp. 9-16.

Stuart, "What's All the Flap About PFO Closure?," *Start-Up: Windhover's Review of Emerging Medical Ventures*, (Nov. 10, 2004), pp. 9-14.

Sztajzel et al., "Patent Foramen Ovale, a Possible Cause of Symptomatic Migraine: A Study of 74 Patients with Acute Ischemic Stroke," *Cerebrovas Dis* (2002) 13: 102-106.

Tang et al., "Quantitative Changes in Collagen Levels Following 830-nm Diode Laser Welding," Lasers Surg Med., vol. 22, No. 4, (1998), pp. 207-211.

Tang et al, "Morphologic Changes in Collagen Fibers after 830 nm Diode Laser Welding," Lasers Surg Med., vol. 21, No. 5 (1997), pp. 438-443.

Thomas, "Patent Foramen Ovale with Right-to-left Shunting: Echocariographic Alternatives," *Eur J Echocariography* (2001) 2:74-75.

Wilmhurst et al., "Effect on Migraine of Closure of Cardiac Right-to-Left Shunts to Prevent Recurrence of Decompression Illness of Illness or Stroke or for Haemodynamic Reasons," *The Lancet*, vol. 356, (Nov. 11, 2000), pp. 1648-1651.

Wilmhurst et al "Relationship between Migraine and Cardiac and Pulmonary Right to Left Shunts," *Clinical Science* (2001) 100:215-220.

Besio et al., "Quantizing the Depth of Bioelectrical Sources for Non-Invasive 3D Imaging," *IJBEM*, vol. 7, No. 2, (2005), 4 pages total.

European Search Report issued Nov. 24, 2010, in Patent Application No. 04758520.3.

European Office Action dated Mar. 11, 2011 issued in counterpart application 04758520.3.

Canadian Office Action dated Mar. 8, 2011 issued in counterpart application 2,519,559.

* cited by examiner

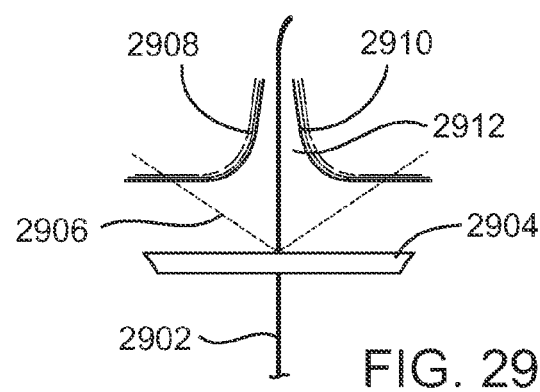
FIG. 29
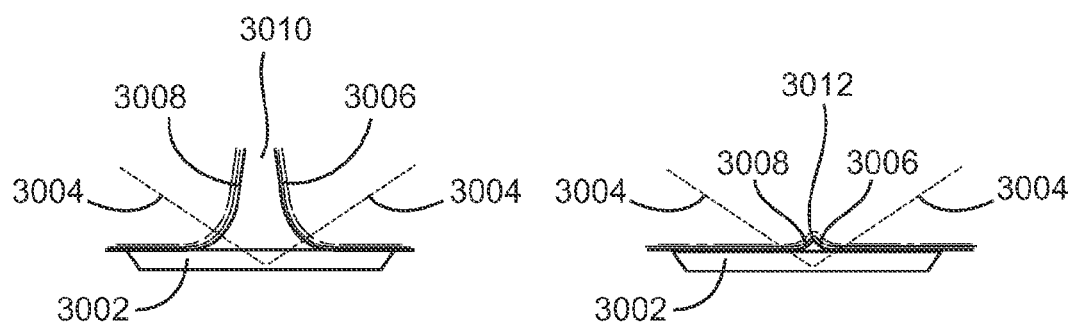
FIG. 30A
FIG. 30B
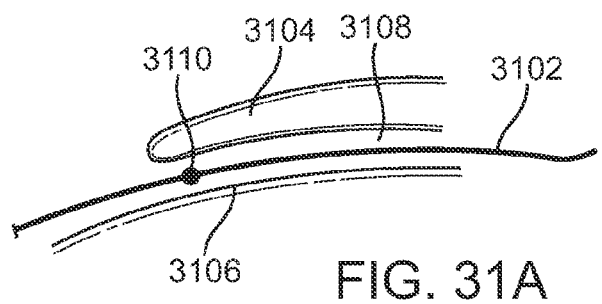
FIG. 31A
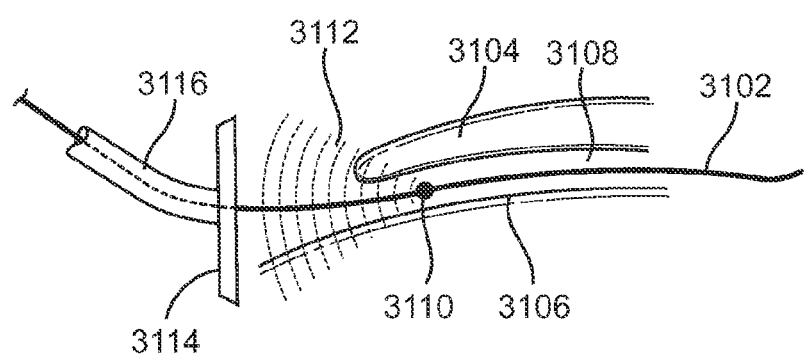
FIG. 31B

METHODS AND APPARATUS FOR CLOSING A LAYERED TISSUE DEFECT

CROSS-REFERENCES TO RELATED APPLICATIONS

This application is a continuation-in-part of U.S. patent application Ser. No. 10/958,533, filed Oct. 4, 2004, which was a divisional of U.S. patent application Ser. No. 10/679,245, filed Oct. 2, 2003, now U.S. Pat. No. 6,939,348, which claimed priority to U.S. Provisional Patent Application No. 60/458,854, filed on Mar. 27, 2003; 60/478,035 filed on Jun. 11, 2003, and 60/490,082 filed on Jul. 24, 2003, the full disclosures of which are incorporated herein by reference. This application is related to U.S. patent application Ser. No. 11/613,422 filed on the same day as the instant application, the entire contents of which are incorporated herein by reference.

BACKGROUND OF THE INVENTION

The invention generally relates to medical devices and methods. More specifically, the invention relates to energy based closure devices and methods for treatment of anatomic defects in human tissue, such as a patent foramen ovale (PFO), atrial septal defect (ASD), ventricular septal defect (VSD), patent ductus arteriosus (PDA), left atrial appendages (LAA), blood vessel wall defects and other defects having layered and apposed tissue structures.

The following is an example of how one particular type of anatomical defect, a PFO, is formed. Fetal blood circulation is very different from adult circulation. Because fetal blood is oxygenated by the placenta, rather than the fetal lungs, blood is generally shunted past the lungs to the peripheral tissues through a number of vessels and foramens that remain patent (i.e., open) during fetal life and typically close shortly after birth. For example, fetal blood passes directly from the right atrium through the foramen ovale into the left atrium, and a portion of blood circulating through the pulmonary artery trunk passes through the ductus arteriosus to the aorta. This fetal circulation is depicted in FIG. 1.

At birth, as a newborn begins breathing, blood pressure in the left atrium rises above the pressure in the right atrium. In most newborns, a flap of tissue closes the foramen ovale and heals together. However, in approximately 20,000 babies born each year in the U.S., the flap of tissue is missing, and the hole remains open as an atrial septal defect (ASD). In a more significant percentage of the population (estimates range from 5% to 20% of the entire population), the flap is present but does not heal together. This condition is known as a patent foramen ovale (PFO). Whenever the pressure in the right atrium rises above that in the left atrium, blood pressure can push this patent channel or tunnel open, allowing blood to flow from the right atrium to the left atrium. Blood shunting also occurs in a patent ductus arteriosus (PDA), where a tubular communication exists between the pulmonary artery and the aorta. The PDA typically closes shortly after birth.

A patent foramen ovale has long been considered a relatively benign condition, since it typically has little effect on the body's circulation. More recently, however, it has been found that a significant number of strokes may be caused at least in part by PFOs. In some cases, a stroke may occur because a PFO allows blood containing small thrombi to flow directly from the venous circulation to the arterial circulation and into the brain, rather than flowing to the lungs where the thrombi can become trapped and gradually dissolve. In other cases, a thrombus might form in the patent channel of the PFO itself and become dislodged when the pressures cause blood to flow from the right atrium to the left atrium. It has been estimated that patients with PFOs who have already had cryptogenic strokes may have an increased risk of having another stroke.

Research is currently being conducted into the link between PFO and stroke. At the present time, if someone with a PFO has two or more strokes, the healthcare system in the United States may reimburse a surgical or other interventional procedure to definitively close the PFO. It is likely, however, that a more prophylactic approach would be warranted to close PFOs to prevent the prospective occurrence of a stroke. The cost and potential side-effects and complications of such a procedure must be low, however, since the stroke event rate due to PFOs is relatively low. In younger patients, for example, PFOs sometimes close by themselves over time without any adverse health effects.

Another highly prevalent and debilitating condition, chronic migraine headache, has also been linked with PFO. Although the exact link has not yet been explained, PFO closure has been shown to eliminate or significantly reduce migraine headaches in many patients. Again, prophylactic PFO closure to treat chronic migraine headaches might be warranted if a relatively non-invasive procedure were available.

Currently available interventional therapies for defect closure are generally fairly invasive and/or have potential drawbacks. One strategy is simply to close a defect during open heart surgery for another purpose, such as heart valve surgery. This can typically be achieved via a simple procedure such as placing a stitch or two across the defect with vascular suture. Performing open heart surgery purely to close an asymptomatic PFO or even a very small ASD, however, would be very hard to justify.

A number of interventional devices for closing defects percutaneously have also been proposed and developed. Most of these devices are the same as or similar to ASD closure devices. They are typically "clamshell" or "double umbrella" shaped devices which deploy an area of biocompatible metal mesh or fabric (ePTFE or Dacron, for example) on each side of the atrial septum, held together with a central axial element, to cover the defect. This umbrella then heals into the atrial septum; the healing response forming a uniform layer of tissue or "pannus" over the device. Such devices have been developed, for example, by companies such as Nitinol Medical Technologies, Inc. (Boston, Mass.) and AGA Medical, Inc. (White Bear Lake, Minn.). U.S. Pat. No. 6,401,720 describes a method and apparatus for thoracoscopic intracardiac procedures which may be used for treatment of PFO.

Although available devices may work well in some cases, they also face a number of challenges. Relatively frequent causes of complications include, for example, improper deployment, device embolization into the circulation, device breakage and device erosion where constant rubbing of the metal frame erodes adjacent tissue, resulting in collateral tissue damage. In some instances, a deployed device does not heal into the septal wall completely, leaving exposed surface which may itself be a nidus for thrombus formation. Furthermore, currently available devices are generally complex and expensive to manufacture, making their use for prophylactic treatment of PFO and other defects impractical. Additionally, currently available devices typically close a PFO by placing material on either side of the tunnel of the PFO, compressing and opening the tunnel acutely, until blood clots on the devices and causes flow to stop Research into methods and compositions for tissue welding has been underway for many years. Of particular interest are technologies developed by McNally et. al., (as shown in U.S. Pat. No. 6,391,049) and Fusion Medical (as shown in U.S. Pat. Nos. 5,156,613; 5,669,934; 5,824,015 and 5,931, 165). These technologies all disclose energy delivery to tissue solders and patches to join tissue and form anastomoses between arteries, bowel, nerves, etc. Also of interest are a number of patents by inventor Sinofsky, relating to laser suturing of biological materials (e.g., U.S. Pat. Nos. 5,725, 522; 5,569,239; 5,540,677 and 5,071,417). Other patents by Laufer (e.g. U.S. Pat. Nos. 5,827,268 and 6,004,316) and publications by Barry (e.g. U.S. Patent Publication No. 2006/0079870) describe the use of energy to shrink or close a layered tissue defect such as a PDA or PFO. None of these disclosures, however, show methods or apparatus suitable for positioning the tissues of the PFO for welding or for welding a PFO with an energy sweeping method, wherein energy is applied to the layered tissue defect at a first position and a second position adjacent to the first position so as to substantially close the layered tissue defect along at least a portion of the defect. It is believed that closing the layered tissue defect in this manner results in a more robust seal than the individual spot welds previously described by others.

Causing thermal trauma to close a patent foramen ovale has been described in two patent applications by Stambaugh et al. (PCT Publication Nos. WO 99/18870 and WO 99/18871). The intent is to eventually cause scar tissue formation which will close the PFO. Blaeser et al. (U.S. Patent Publication No. 2003/0208232), describes causing trauma, or abrading, and holding the abraded tissue in apposition to allow the tissue to heal together. Using such devices and methods, the PFO typically remains patent immediately after the procedure, or abrasion, and only closes sometime later, or is treated and then held together to heal over time. Frequently, scar tissue may fail to form or may form incompletely, resulting in a still patent PFO.

In addition to PFOs, a number of other anatomic tissue defects, such as other ASDs, ventricular septal defects (VSDs), patent ductus arteriosus (PDA), aneurysms and other blood vessel wall defects, atrial appendages and other naturally occurring cavities within which blood clots can form, and the like cause a number of different health problems (note that the term "defect" or "layered tissue defect" may include a naturally occurring structure that results a potential health risk such as the clot forming in the atrial appendage). U.S. Patent Application No. 2004/0098031 (Van der Burg), and U.S. Pat. No. 6,375,668 (Gifford) and U.S. Pat. No. 6,730,108 (Van Tassel et al.), the full disclosures of which are incorporated herein by reference, disclose a variety of techniques and devices for treating anatomic defects. In addition, the inventors of the present invention have described a number of improved devices, methods and systems for treating a PFO, many of which may be adapted for treating other anatomic tissue defects as well. For example, related patent applications assigned to the assignee of the present invention include U.S. patent application Ser. No.: 10/665,974 filed on Sep. 16, 2003; Ser. No. 10/679,245 filed Oct. 2, 2003; Ser. No. 10/952, 492 filed Sep. 27, 2004; Ser. No. 10/873,348 filed on Jun. 21, 2004; Ser. No. 11/049,791 filed on Feb. 2, 2005; Ser. No. 10/787,532 filed Feb. 25, 2004; Ser. No. 10/764,148 filed Jan. 23, 2004; Ser. No. 10/811,228 filed Mar. 26, 2004; Ser. No. 11/403,038 filed Apr. 11, 2006; Ser. No. 11/403,052 filed Apr. 11, 2006; Ser. No. 11/402,489 filed Apr. 11, 2006; and U.S. Provisional Application 60/670,535 filed Apr. 11, 2005, the full disclosures of which are incorporated herein by reference.

Despite improvements made thus far, it would be advantageous to have even further improved methods, systems, and apparatus for treating anatomic tissue defects such as PFOs and the other anatomic structures mentioned above. Ideally, such methods and apparatus would help position a closure device so that a complete seal of a PFO or other anatomic tissue defect can be achieved reliably and in a predictable fashion. Also, such devices and methods would leave no foreign material (or very little material) in a patient's heart. Furthermore, such methods and apparatus would preferably be relatively simple to manufacture and use, thus rendering prophylactic treatment of PFO and other tissue defects a viable option. Ideally, such methods and apparatus could also be used in a minimally invasive manner, with low profile for ease of introduction into the body, while effectively closing the PFO quickly, effectively and without causing damage to other portions of the body. When success of the closure procedure can be well predicted, physicians are more likely to recommend such a procedure prophylacticly. At least some of these objectives will be met by the present invention.

BRIEF SUMMARY OF THE INVENTION

The present invention generally provides devices and methods for treating patent foramen ovale (PFO). More specifically, the devices and methods involve advancing a catheter device to a position in the heart for treating the patent foramen ovale and applying energy to (or removing energy from) tissues at a first position adjacent a PFO and a second position adjacent to the first position so as to substantially close the PFO acutely. In some embodiments of the method, multiple passes of the catheter may be employed. For example, a first pass may be utilized in order to apply energy and shrink the tissues followed by a second, third or additional pass of the catheter to substantially close or seal the PFO. By "substantially," it is meant that a stable tissue bridge will be formed across the PFO, which will withstand physiologic pressures. A substantially closed PFO, however, may still have one or more small gaps or openings, which will in at least some cases close over time via the healing process. By "acutely," it is meant that the PFO is substantially closed when the closure procedure is completed. Thus, acute closure distinguishes devices and methods of the present invention from prior protocols, which rely on delayed PFO closure via tissue healing and scarring. "Acutely," for purposes of this application, does not mean temporarily, since devices and methods of the present invention will typically provide for permanent (or at least long-term) PFO closure.

The phrase "tissues adjacent a PFO," or simply "PFO tissues," for the purposes of this application, means any tissues in, around or in the vicinity of a PFO which may be used or manipulated to help close the PFO. For example, tissues adjacent a PFO include septum primum tissue, septum secundum tissue, atrial septal tissue lateral to the septum primum or septum secundum, tissue within the tunnel of the PFO, tissue on the right atrial surface or the left atrial surface of the atrial septum and the like. By "application or removal" of energy, it is meant that energy may be transferred either to or from PFO tissues. In various embodiments, any of a number of energy transfer devices and forms of energy may be used to provide such energy transfer. Types of energy used may include, for example, radiofrequency, cryogenic, laser, ultrasound, resistive heat, microwave and the like.

Application of energy to (or removal of energy from) tissues to substantially close the PFO acutely may sometimes be referred to as "tissue welding." Preferably, tissue welding methods of the present invention will be performed without using tissue soldering material or other foreign material. In some embodiments, however, it may be advantageous to use one or more solder materials. Various solders and other tissue soldering matrices are described more fully in U.S. patent application Ser. No. 10/665,974 the contents of which are incorporated herein by reference. Examples of tissue solders or adhesives which may be used include, but are not limited to, autologous blood, albumin, collagen, fibrin, cyanoacrylates, mussel byssus adhesives, polymer hot melt adhesives and the like.

In some embodiments of the present invention, devices and methods further provide for bringing tissues adjacent a PFO together (or "apposing" tissues). In various embodiments, tissues may be apposed before, during and/or after application or removal of energy to the tissues. Generally, energy application or removal will act to denature collagen in the PFO tissues. If the tissues are apposed before and/or during denaturation and/or while the collagen in the tissues is allowed to renature, the collagen in once-separated tissues binds together to bring the tissues together. Therefore, although not required, some embodiments of the invention include one or more devices for bringing (and possibly holding) tissues together before, during and/or after energy application or removal. Such devices include, for example, PFO tissue covering members, which may also be suction or vacuum application members, expandable members within the PFO tunnel, distal tip members for contacting a left atrial surface of PFO tissue and the like. By providing for substantial, acute closure of a PFO, devices and methods of the invention may be advantageous for preventing stroke, treating migraine headaches and/or preventing or treating other medical conditions caused or exacerbated by PFO.

In a first aspect of the present invention, a method for closing a layered tissue defect comprises inserting a first closure device into the layered tissue defect and positioning the first closure device so that at least a portion of the closure device is contacting the layered tissue defect. Energy is applied to the layered tissue defect with the first closure device at a first position and also a second position which is adjacent to the first position so as to substantially close the layered tissue defect along at least a portion of the defect. The first closure device is then removed from the layered tissue defect. In some cases, removing the closure device comprises retracting the closure device into the elongate flexible member.

In a second aspect of the present invention, a method for closing a layered tissue defect comprises inserting a first closure device into the layered tissue defect and positioning the first closure device so that at least a portion of the closure device is contacting the tissue defect. Applying energy to the tissue defect while sweeping the first closure device from a first position to a second position substantially closes the layered tissue defect along at least a portion of the defect. The first closure device is then removed from the defect. Sometimes, the method may further comprise repositioning the first closure device so that at least a portion of the device is contacting the layered tissue defect and reapplying energy to the defect while retracting or sweeping the first closure device from a first position to a second position so as to close the layered tissue defect along at least a portion of the defect. The device may then be removed from the layered tissue defect.

Sometimes the method may further comprise positioning a second closure device so that that the second device is contacting the layered tissue defect. Applying energy to the tissue defect while retracting the second closure device from a first position to a second position closes the layered tissue defect along at least a portion of the defect. The second closure device is then removed from the tissue defect.

Often, the layered tissue defect is a patent foramen ovale having a tunnel with a right atrial opening and a left atrial opening. Furthermore, the first position is at a location within the layered tissue defect that is closer to the left atrial opening and the second position is at a location within the defect that is closer to the right atrial opening.

In another aspect of the present invention, a method for closing a layered tissue defect comprises inserting a first closure device into the layered tissue defect and positioning the closure device so that at least a portion of the closure device is contacting the layered tissue defect. Energy is applied to the layered tissue defect with the closure device, while the closure device is retracted along a path so as to substantially close the layered tissue defect along at least a portion of the path. The closure device is then removed from the layered tissue defect. Removing the closure device may additionally comprise retracting the closure device into the elongate flexible member.

The layered tissue defect may be a patent foramen ovale, an atrial septal defect, a ventricular septal defect, a patent ductus arteriosus, left atrial appendage, or other defect having layered and apposed tissue structures. In the case of a patent foramen ovale (PFO), the PFO typically has a tunnel with a right and left atrial openings and the first position is at a location within the layered tissue defect that is closer to the left atrial opening while the second position is also at a location within the layered tissue defect and is closer to the right atrial opening. In some cases, a second closure device may be inserted into the layered tissue defect from a direction opposite that of the first closure device.

The closure device often comprises an electrode and energizing the closure device comprises delivering monopolar energy or bipolar energy or combinations thereof. Energizing the closure device may also comprise delivering different types of energy such as one of radiofrequency, cryogenic, resistive heat, direct heat, ultrasound, microwave and laser.

Also, in the method, positioning the closure device may comprise applying a compressive force so that at least a portion of the closure device is apposed with the layered tissue defect. A vacuum may be applied so that at least a portion of the closure device is apposed with the layered tissue defect. Often, removing the closure device comprises retracting the closure device as the closure device collapses to a reduced profile. Additionally, in both aspects of the method a cross-linking agent may be delivered to the layered tissue defect and the method may comprise imaging the layered tissue defect with, for example, intravascular ultrasound (IVUS). In some cases, imaging the layered tissue defect will be from within the defect, looking outward toward the right side of a patient's heart.

In another aspect of the present invention, an apparatus for closing a layered tissue defect comprises an elongate flexible member having both proximal and distal ends and an energy transmission member disposed near the distal end of the elongate flexible member. This energy transmission member may have an insulated region and applies energy to the layered tissue defect at a first position and also a second position that is adjacent to the first position so as to substantially close the layered tissue defect along at least a portion of the defect. In some cases, the apparatus comprises an elongate flexible delivery catheter and the energy transmission member is adapted to close a distal portion of the layered tissue defect. Often the energy transmission member is collapsible to a reduced profile. The layered tissue defect may be a patent foramen ovale, an atrial septal defect, a ventricular septal defect, a patent ductus arteriosus, left atrial appendage, or other defect having layered and apposed tissue structures.

The energy transmission member in the apparatus often comprises an electrode adapted to deliver monopolar or bipolar energy or combinations thereof. The energy may be one of radiofrequency, cryogenic, resistive heat, direct heat, ultrasound, microwave and laser. Additionally, the apparatus may further comprise a force applying member near the distal end of the elongate flexible member which is adapted to apply a compressive force so that at least a portion of the apparatus is apposed with the layered tissue defect. A lateral force may also be applied. Alternatively, the force applying member may be adapted to apply a vacuum so that at least a portion of the apparatus is apposed with the layered tissue defect.

In one embodiment of the apparatus, the apparatus further comprises an intravascular ultrasound member near the distal end of the elongate flexible member and adapted to image the layered tissue defect. This ultrasound member may be integral with the elongate flexible member or it may be alongside the elongate flexible member. Ultrasound markers adjacent to the energy transmission member and adapted to enhance apparatus visibility during ultrasound imaging may also be employed in the apparatus.

In other embodiments the energy transmission member comprises a pair of elongated prongs with optional vacuum apertures and an optional stopping element, both which may be disposed on the energy transmission member. In other embodiments, the elongate flexible member comprises a guide wire which may comprise a variable resistor and may have insulated portions. In still other embodiments, the energy transmission member may comprise an expandable member with or without a backstopping element. The expandable member can be a balloon which may have an electrode or comprise conductive materials. In some embodiments, the energy transmission member comprises a plurality of electrodes disposed on the balloon. In still other embodiments, the expandable member is a wire form or wire-like basket, typically adapted to collapse to a lower profile upon application of energy to the layered tissue defect. Some embodiments may further comprise a second wire form or wire-like basket adjacent to the first wire-like basket. Both wire forms may be coaxial with one another and they may move independently of one another or they may be axially fixed relative to each other. Both wire forms may be partially or totally insulated. The wire forms are often adjacent to the distal end of the elongate flexible member and they often are wire-like baskets, braids, coils, meshes and they may be ovoid, trumpet, bulb, rectangular or cylindrically shaped and portions of the wire form may be insulated. Optionally, the wire form may be adapted to be retracted into the elongate flexible member or a guide catheter. In many of these embodiments, the energy transmission member is collapsible to a reduced profile.

In some embodiments, the energy transmission member is of unitary construction. In other embodiments, the energy transmission member comprises a plurality of retractable electrodes while in other embodiments the apparatus further comprises a second elongate flexible member having both proximal and distal ends along with a second energy transmission member. The second energy transmission member is deployable from the second elongate flexible member and applies energy to the layered tissue defect at a first position and a second position adjacent to the first position so as to substantially close the layered tissue defect along at least a portion of the defect. Often, this second energy transmission member is retracted away from the first energy transmission member.

In other embodiments the energy transmission member comprises at least one collapsible electrode that is adapted to collapse to a lower profile as the layered tissue defect closes around the collapsible electrode. Often, one or more thermocouples are disposed adjacent to the electrodes. In some cases, the apparatus may comprise a sock covering the energy transmission member, and the sock comprises an implantable material such as collagen. The sock may also comprise a lubricious inner liner adapted to facilitate separation of the sock from the energy transmission member. The apparatus may also comprise means for delivering collagen to the layered tissue defect with or without a cross-linking agent such as glutaraldehyde.

In still other embodiments the energy transmission member comprises an adjustable loop that may have at least one electrode. In other embodiments the energy transmission member comprises a plurality of flexible elongated wires, while other energy transmission members are fan shaped or cone shaped. Typically, the loop, flexible elongated wires, cone or fan shaped energy transmission members are collapsible into a reduced profile. Often, these fan shaped or cone shaped energy transmission members are retractable into the elongate flexible member. Some embodiments may also comprise a backstop element that limits motion of the closure device in the layered tissue defect, and can also serve a dual purpose as an energy return member.

These and other embodiments are described in further detail in the following description related to the appended drawing figures.

BRIEF DESCRIPTION OF THE DRAWING FIGURES

Figure 1:
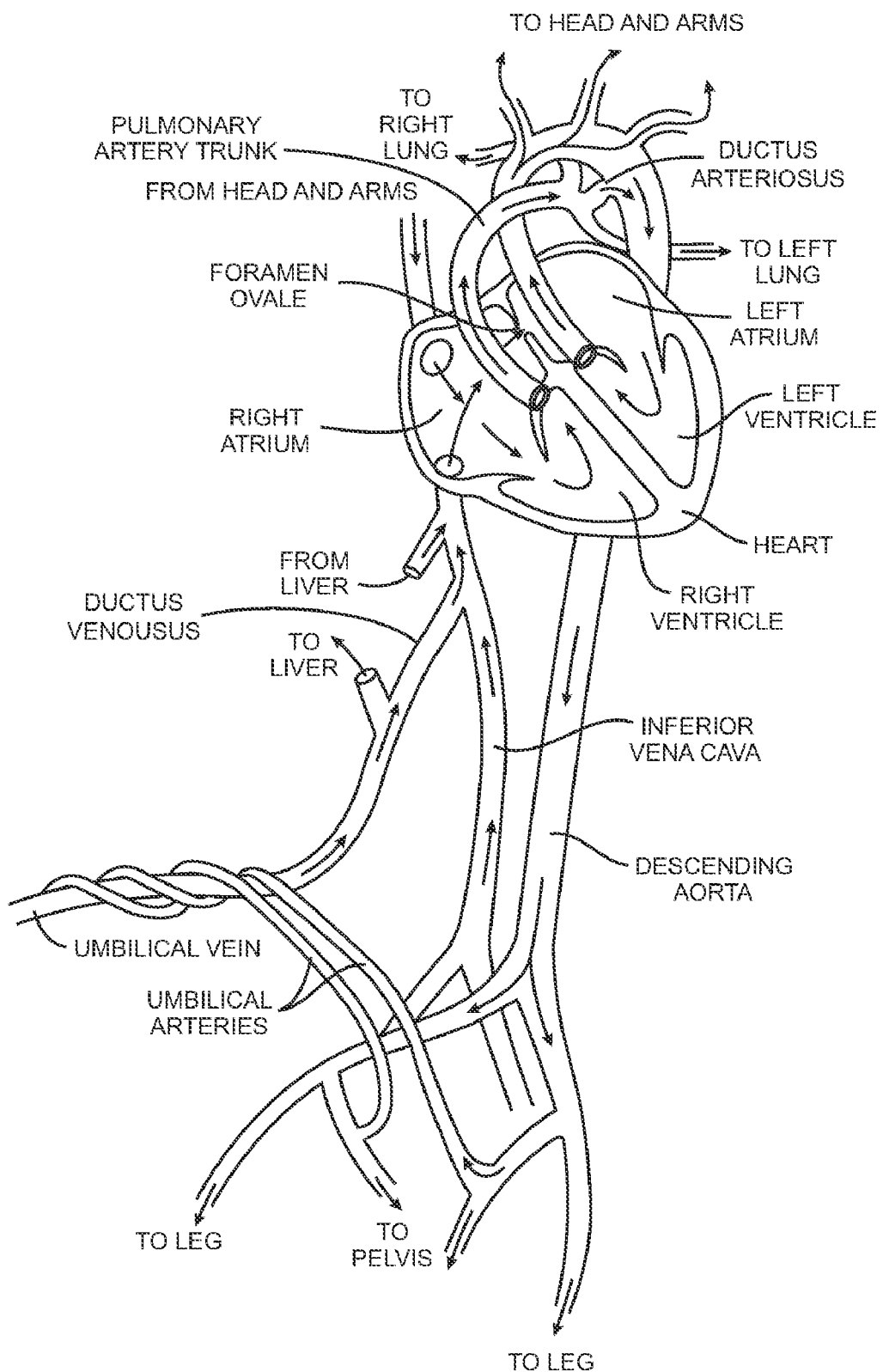
FIG. 1 is a diagram of the fetal circulation.
Figure 11A:
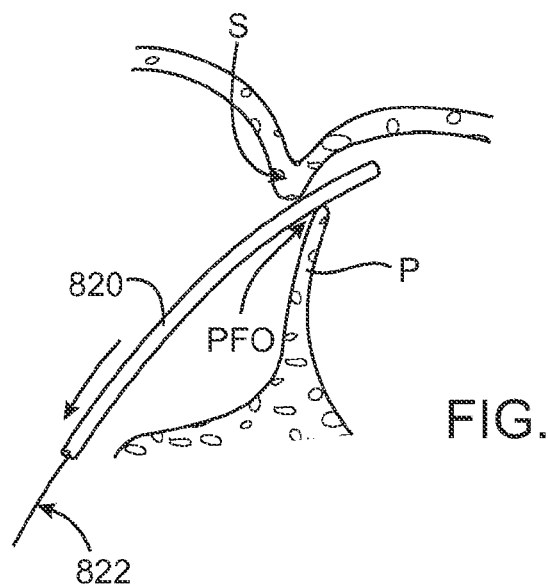
Figure 12A:
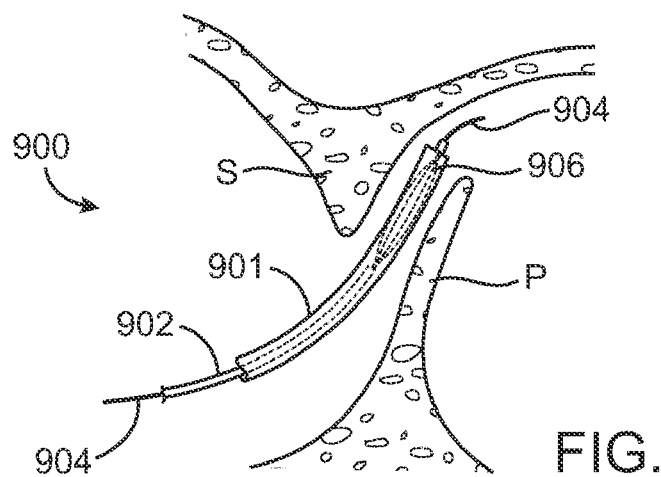
Figure 12B:
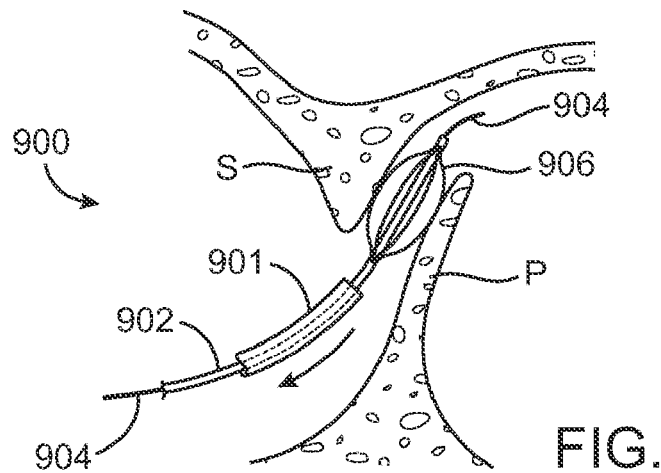
Figure 13:
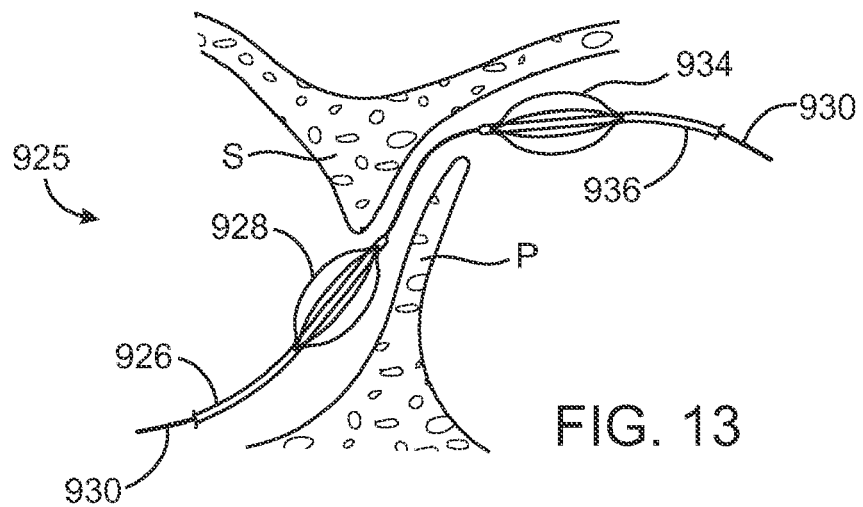
Figure 15:
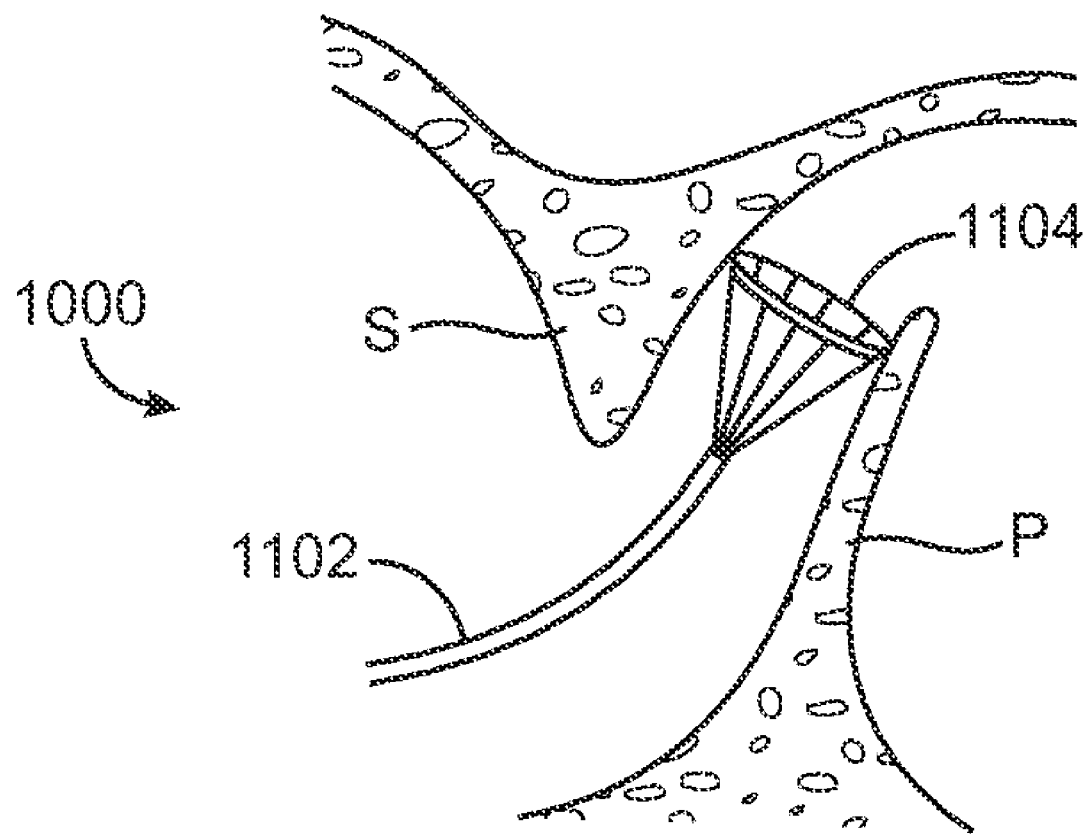
Figure 19:
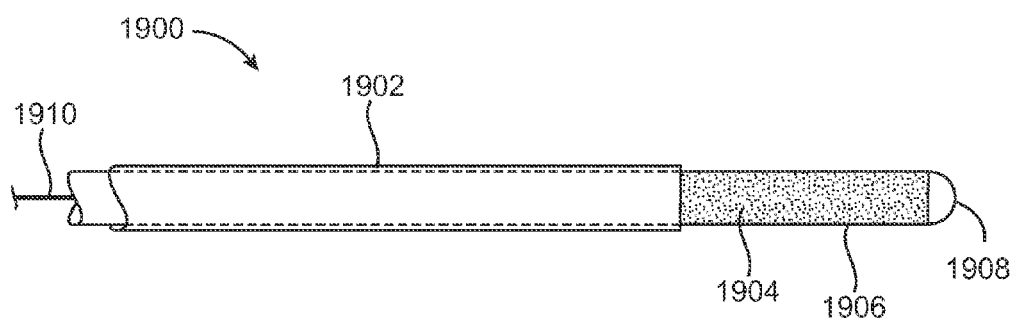
Figure 20:
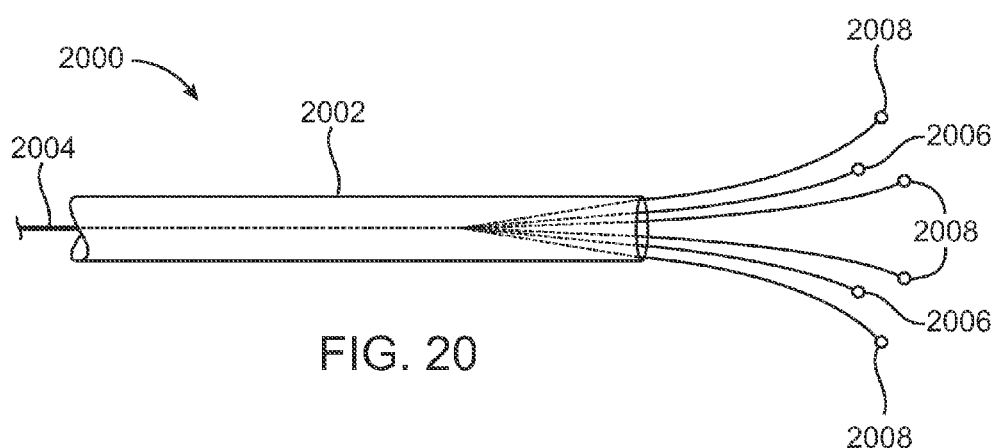
Figure 21A:
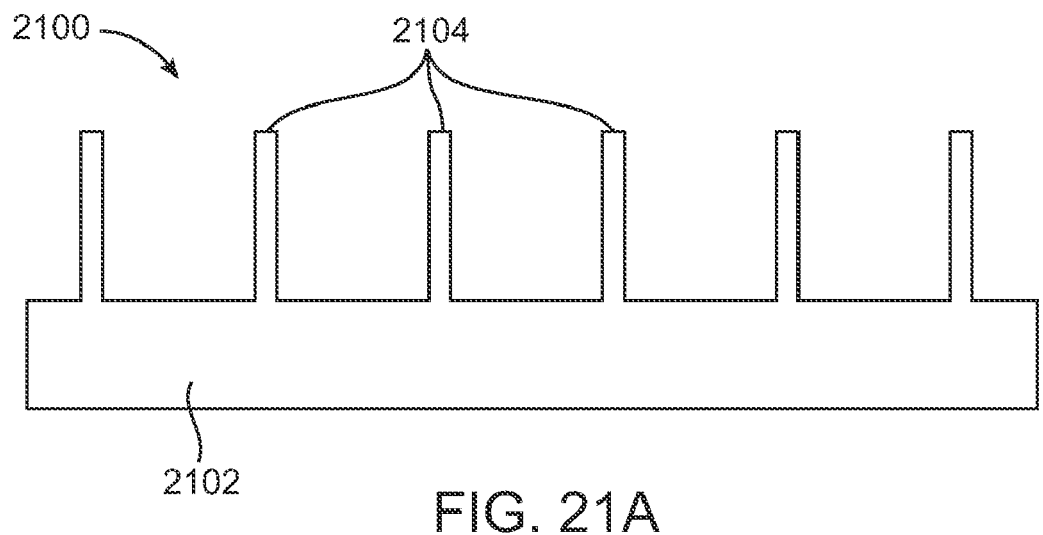
Figure 21B:
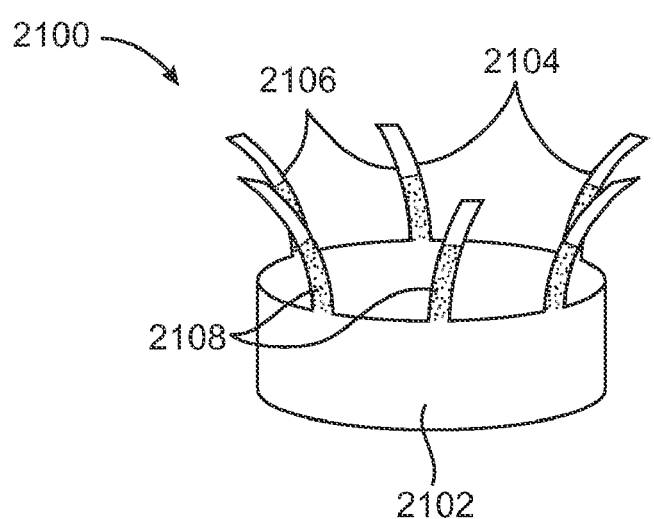
Figure 21C:
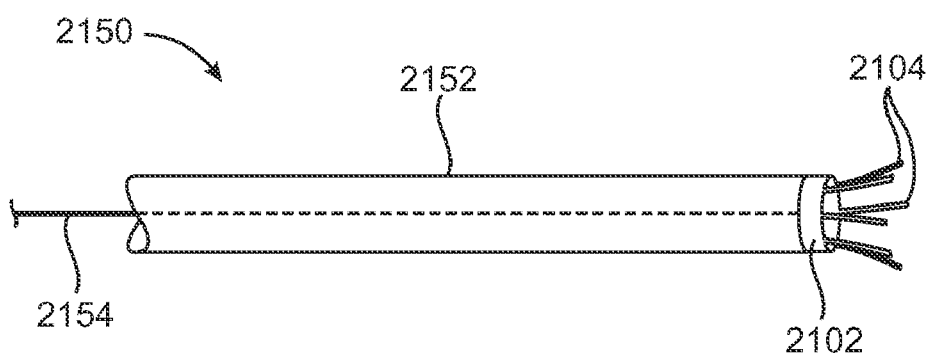
Figure 22A:
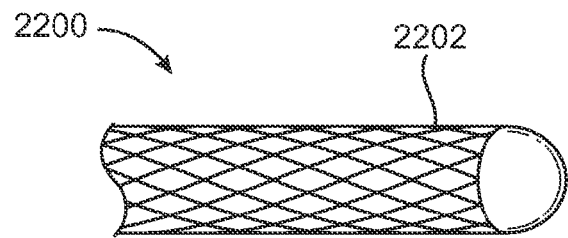
Figure 22B:
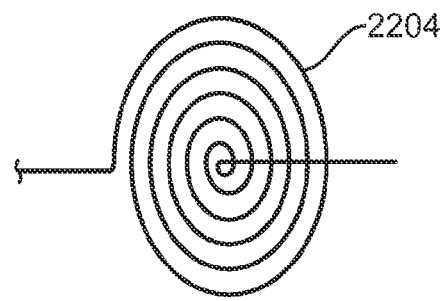
Figure 22C:
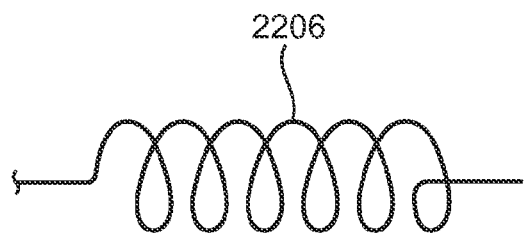
Figure 23:
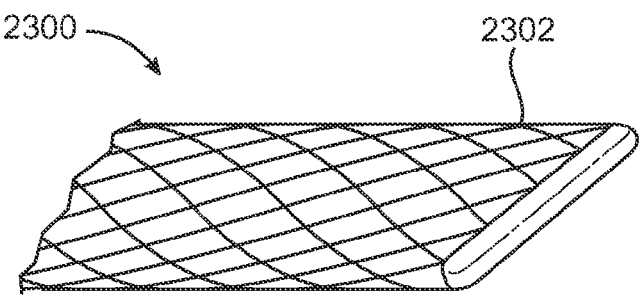
Figure 24A:
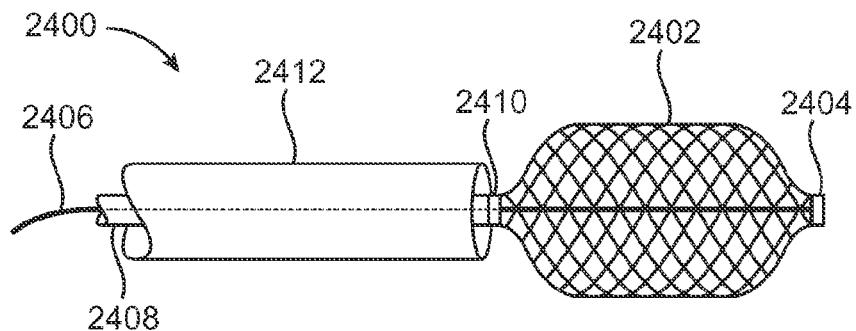
Figure 24B:
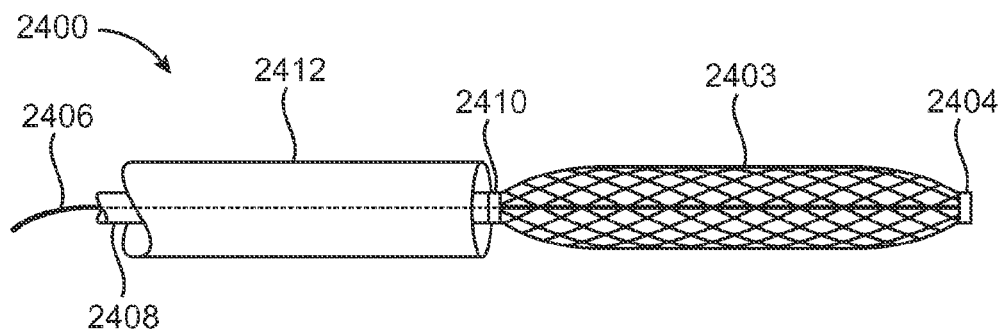
Figure 26:
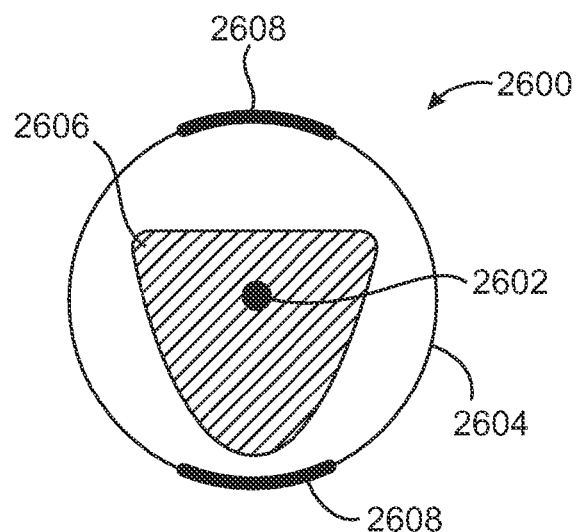
Figure 27:
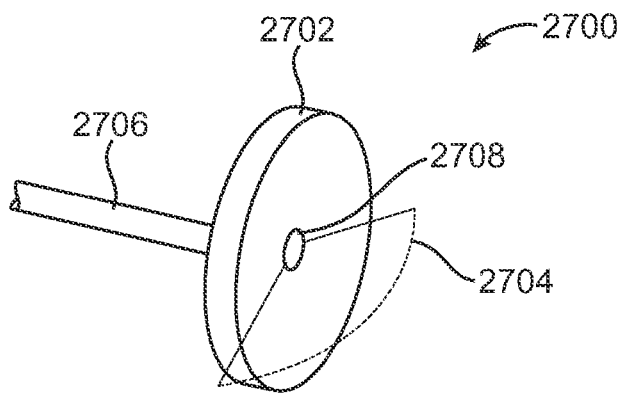
Figure 28:
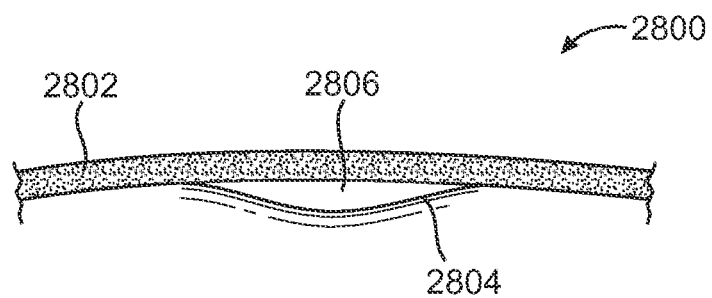

FIG. 11A-1 LE illustrate a method for closing a layered tissue defect;

FIGS. 12A-12B shows an embodiment of a closure device with a wire-like basket in both the undeployed and deployed states;

FIG. 13 shows an embodiment where two wire-like baskets are used to treat a layered tissue defect;

FIGS. 14A-14D illustrates a closure device having a fan shaped energy transmission member;

FIG. 15 shows another embodiment with a cone shaped energy transmission member;

FIGS. 16A-18 show basket-like embodiments;

FIG. 19 shows an insulated guide wire embodiment;

FIG. 20 illustrates the use of thermocouples adjacent to electrodes;

FIGS. 21A-21C show how electrodes may be formed from a flat sheet;

FIGS. 22A-22C show wire braided devices having various configurations;

FIG. 23 shows another wire braided device;

FIGS. 24A-24B show how the shape of a wire braided device may be adjusted;

FIGS. 25A-25F illustrate a method of closing a PFO in accordance with one embodiment of the present invention;

FIG. 26 illustrates the use of ultrasound markers on a closure device;

FIG. 27 shows horizontal sweep of an ultrasound transducer;

FIG. 28 shows a PFO as imaged with ultrasound;

FIG. 29 shows how ultrasound may be used to determine guide wire position in the PFO tunnel;

FIGS. 30A-30B shows how ultrasound may be used to visualize a patent PFO tunnel and a closed PFO tunnel; and FIGS. 31A-31B illustrate how an ultrasound element on a guide wire may be used to look back from the PFO tunnel into the right atrium.

DETAILED DESCRIPTION OF THE INVENTION

Devices and methods of the present invention generally provide for patent foramen ovale (PFO) treatment through application or removal of energy. Methods involve advancing a catheter device to a position in the heart for treating the PFO and applying energy to (or removing energy from) tissues adjacent a PFO to substantially close the PFO acutely. Terms such as "substantially," "acutely," and "tissues adjacent the PFO" are defined above in the Brief Summary of the Invention. Devices of the invention generally include an elongate flexible member having a proximal end and a distal end and at least one energy transmission member deployable from the elongate flexible member for applying energy to or removing energy from tissues adjacent the PFO.

As mentioned above in the background section, FIG. 1 is a diagram of the fetal circulation. The foramen ovale is shown, with an arrow demonstrating that blood passes from the right atrium to the left atrium in the fetus. After birth, if the foramen ovale fails to close (thus becoming a PFO), blood may travel from the right atrium to the left atrium or vice versa, causing increased risk of stroke, migraine and possibly other adverse health conditions, as discussed above.

Figure 2A:
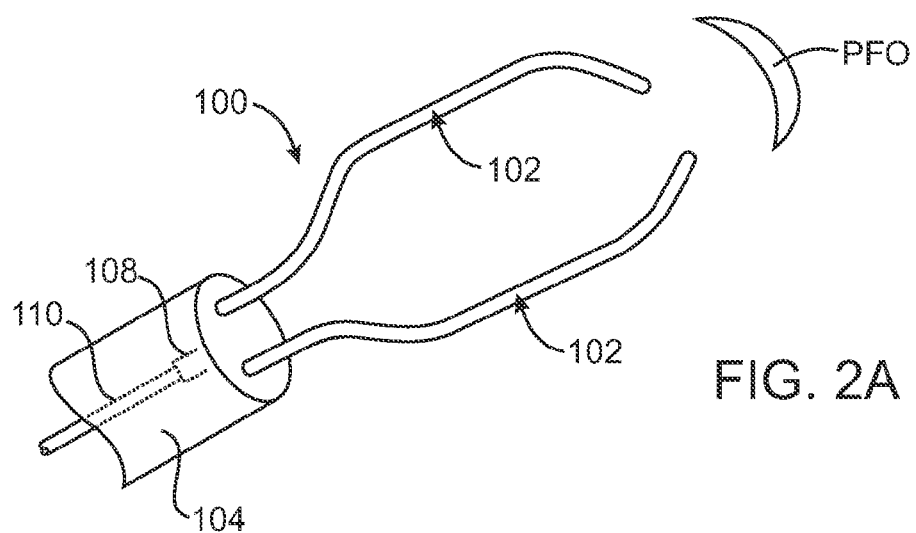
FIGS. 2A-2F show embodiments of a layered tissue defect closure device with and without vacuum apertures and an optional staple or clip.
Figure 2B:
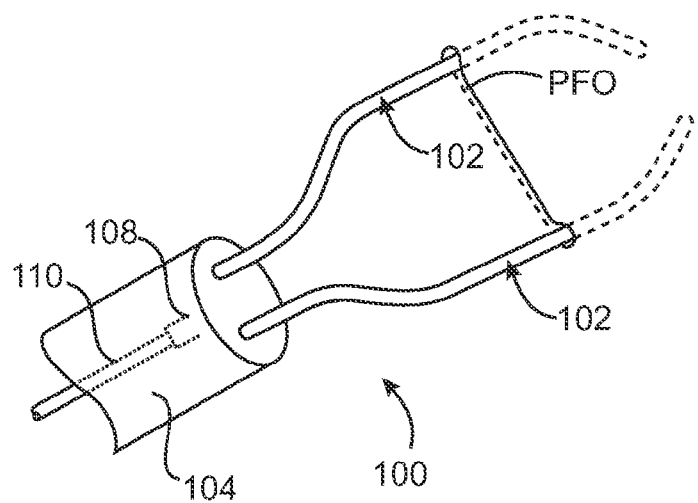
Figure 2C:
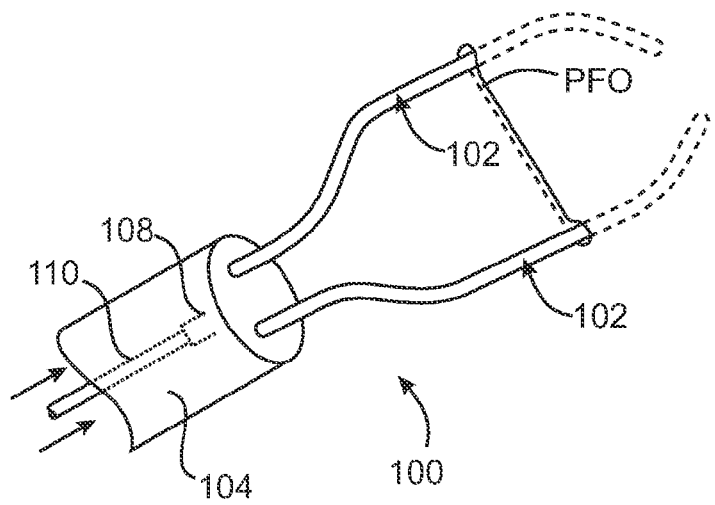
Figure 2D:
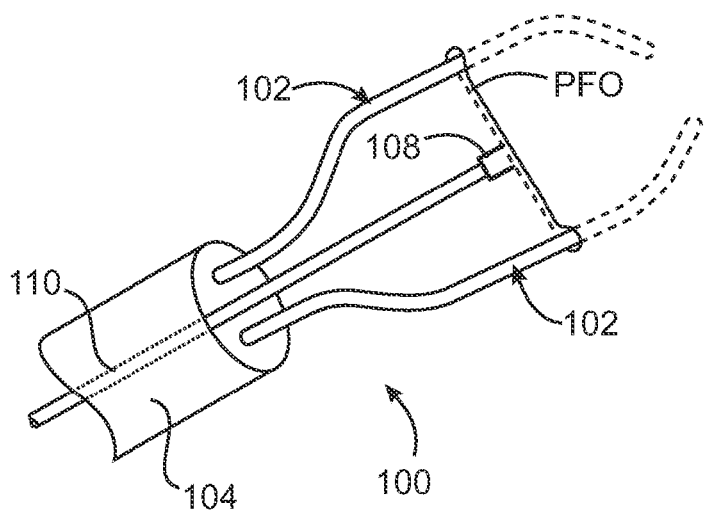
Figure 2E:
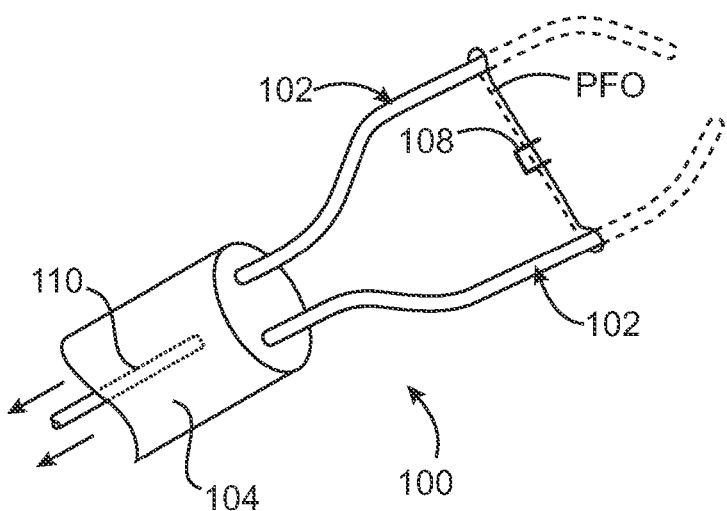

Referring now to FIGS. 2A-2E, one embodiment of a PFO closure device 100 comprises a catheter 104 and a pair of flexible spring arms or prongs 102 attached to catheter 104. FIG. 2A shows an optional clip or staple 108 coupled to an inner shaft 110 and that is deployable from catheter 104. In FIG. 2B, the flexible spring arms 102 are inserted into the PFO and they impart a lateral force to the PFO tissue. This lateral force serves two purposes: it rotationally orients a delivery catheter relative to the PFO, and it brings together the septum primum and septum secundum thereby positioning the PFO in its naturally closed position. Once it is held in its naturally closed position, as shown in FIG. 2B, a penetrating staple 108, non-penetrating clip or other suitable device may be deployed from catheter 104 by advancing inner shaft 110 as seen in FIG. 2C until the staple 108 contacts the tissues of the PFO, shown in FIG. 2D. In FIG. 2E the staple 108 is applied to permanently hold together and seal the PFO and inner shaft 110 is retracted back into catheter 104. Alternatively, the primum and secundum may be welded together by delivering energy to either or both of the primum and septum secundum.

Figure 2F:
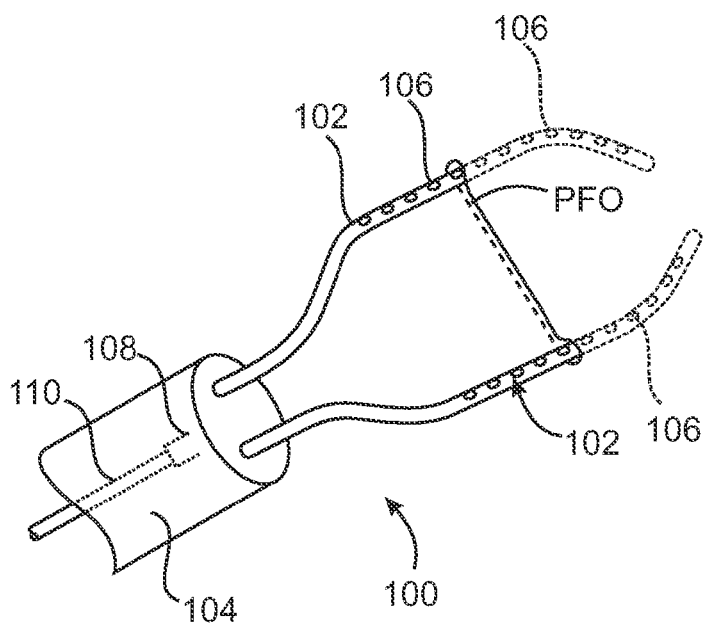

In a preferred embodiment, once the flexible spring arms, or prongs are inserted into the PFO, energy is applied. Energy continues to be delivered to the tissue defect as the flexible spring arms are retracted from the defect, thus substantially sealing the defect. Radiofrequency energy is preferable, either monopolar or bipolar or combinations thereof, although other forms of energy may also be used to close the defect. Examples of other forms of energy include cryogenic, resistive heat, ultrasound, microwave and laser. FIG. 2F illustrates another embodiment similar to that depicted in FIGS. 2A-2E, yet in this new embodiment, vacuum apertures 106 are disposed on the flexible spring arms. Thus, a vacuum may be applied to the PFO tissues to help appose tissue against the flexible spring arms during energy delivery and retraction of the device.

Although the embodiment depicted in FIGS. 2A-2F and many of the embodiments described below include one or more tissue apposition members, devices of the present invention do not require such members. In some embodiments, as mentioned above and as set forth in the claims, devices may include a catheter device having one or more energy transmission members for applying or removing energy, without any components designed for bringing the tissues together. Therefore, although much of the following discussion focuses on embodiments including tissue apposition members and the like, such members are not required.

Figure 3A:
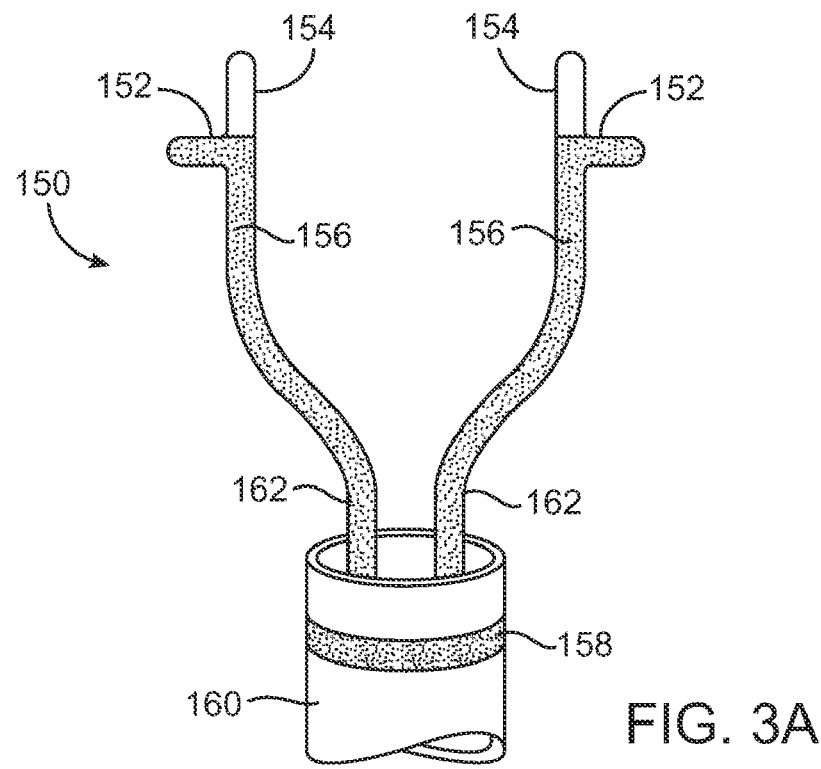
FIGS. 3A-3B shows alternative embodiments of a closure device having a backstop.

Referring now to FIG. 3A, devices such as those described in FIGS. 2A-2C will most preferably make use of monopolar radiofrequency (RF) energy transmitted from the conductive elements of the treatment apparatus, through the patient, completing the circuit to a ground pad affixed to the external skin of the patient. Control systems within the energy delivery systems may automatically stop energy delivery upon detecting a change in condition of energy delivery, for instance an increase in electrical resistance or impedance within the closure device and/or tissues, an increased energy draw from the treatment apparatus, or a sudden temperature rise. In other embodiments, bipolar RF energy may be transmitted from the treatment apparatus. Alternatively, other forms of energy may be applied to one or more closure devices and/or to tissues adjacent a PFO, such as but not limited to resistive heating, heat energy, ultrasound, microwave, laser or cryogenic energy.

Figure 3B:
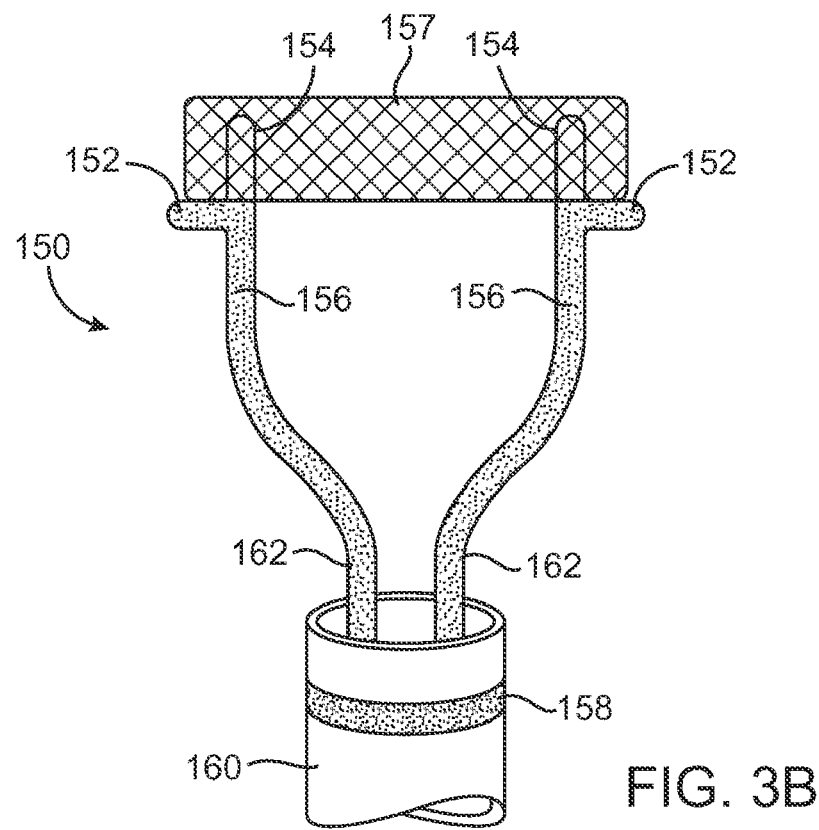

FIG. 3A shows a distal end of one embodiment of a catheter 150 having treatment apparatus 162 comprising two conductive elements extending from a delivery sheath 160, each having an insulated proximal portion 156, a positive stop 152, and an uninsulated distal energy transmission portion 154. Catheter 150 may also include a ground site 158 for bipolar use. Positive stops 152 engage the peripheral limits of the PFO in order to allow passage of treatment apparatus 162 to a predetermined depth within the PFO. The multiple conductive elements 154 may be actuatable by spring-action or through positive mechanical means such as hinges, so that the multiple conductive elements 154 can expand and apply lateral forces to the PFO, stretching the tissue of the septum primum and septum secundum apart, thereby bringing the edges of these tissue structures into apposition. Once the closure device 150 is properly positioned within the PFO, energy is applied to the tissue as the catheter 150 is withdrawn from the PFO, thereby substantially sealing the tissue defect. Optionally, in this embodiment, an additional implantable closure device 157 of the types described in U.S. patent application Ser. No. 10/665,974 which has previously been incorporated by reference, may span the distance between the uninsulated energy transmission portions 156 of the conductive elements. This additional implantable closure device 157 is shown in FIG. 3B.

Figure 4:
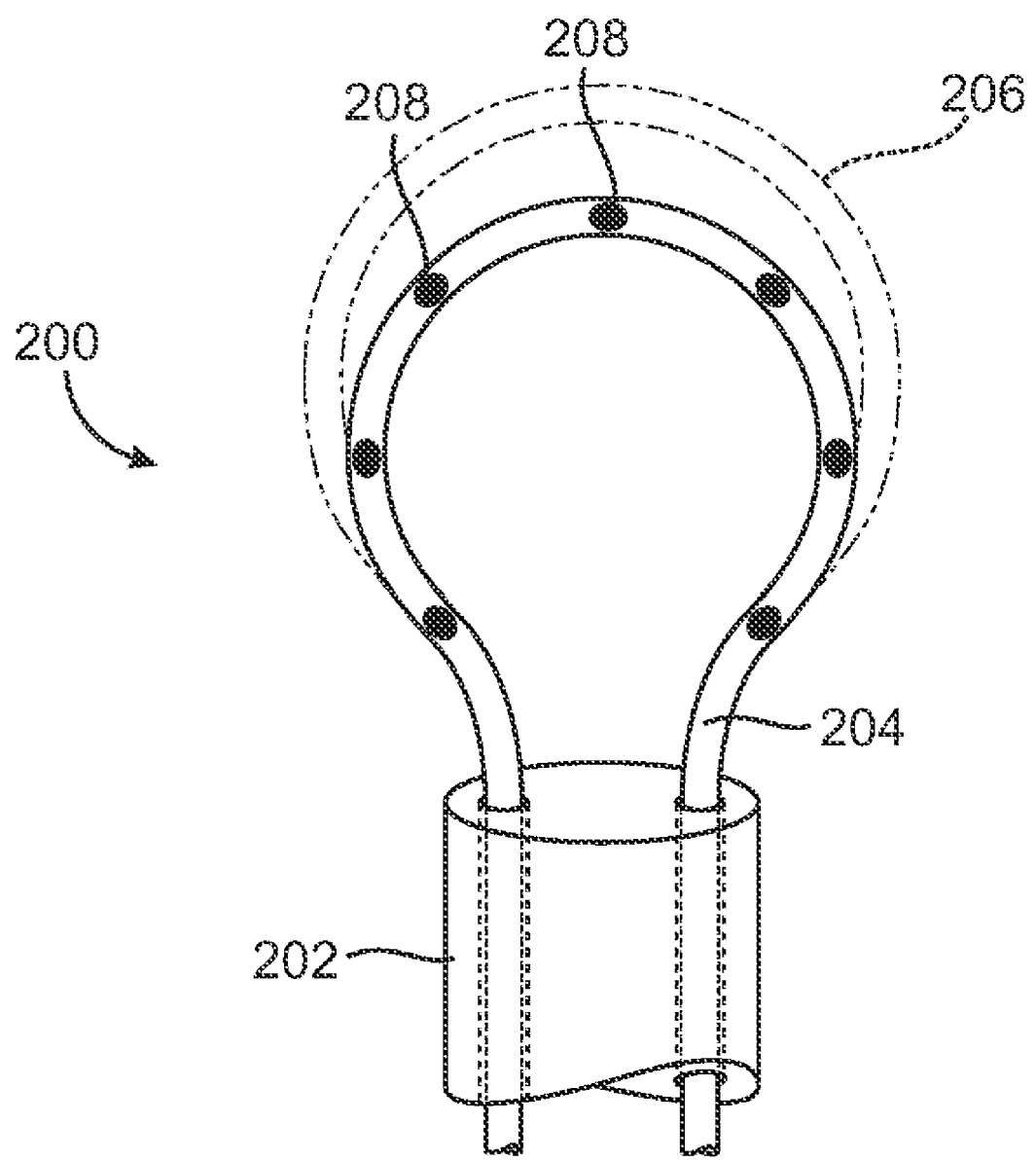
FIG. 4 illustrates an adjustable loop closure device with electrodes.

FIG. 4 illustrates another embodiment of a closure device 200. In FIG. 4, closure device 200 comprises an adjustable loop element 204 which is deployed from a catheter shaft 202 and retractable into the shaft 202. FIG. 4 depicts adjustable loop 204 as a single electrode, although it may comprise multiple electrodes and insulation such as parylene may be deposited on various portions of the electrodes to control the conductive regions or individual electrodes may be selectively activated. Adjustable loop 204 may be a fixed structure or it may be a dynamic structure. Optionally, suction can be applied from within the lumen of a hollow loop to help appose tissue in the defect while energy is applied. Deploying the adjustable loop element 204 allows the size of the loop to be increased or decreased to appose with the PFO tissue defect. In FIG. 4, the loop is enlarged 206 to accommodate a larger PFO tunnel. Electrodes 208 disposed on the adjustable loop 206 permit energy to be delivered from the closure device 200 to the layered tissue defect. In operation, as energy is applied to the PFO the loop can be retracted so that the loop element does not become stuck or welded to the tissue. Typical materials used to fabricate the adjustable loop 204 include a shape memory alloy such as nitinol formed of a nickel titanium alloy and spring temper stainless steels, as well as other materials such as polymers.

Figure 5A:
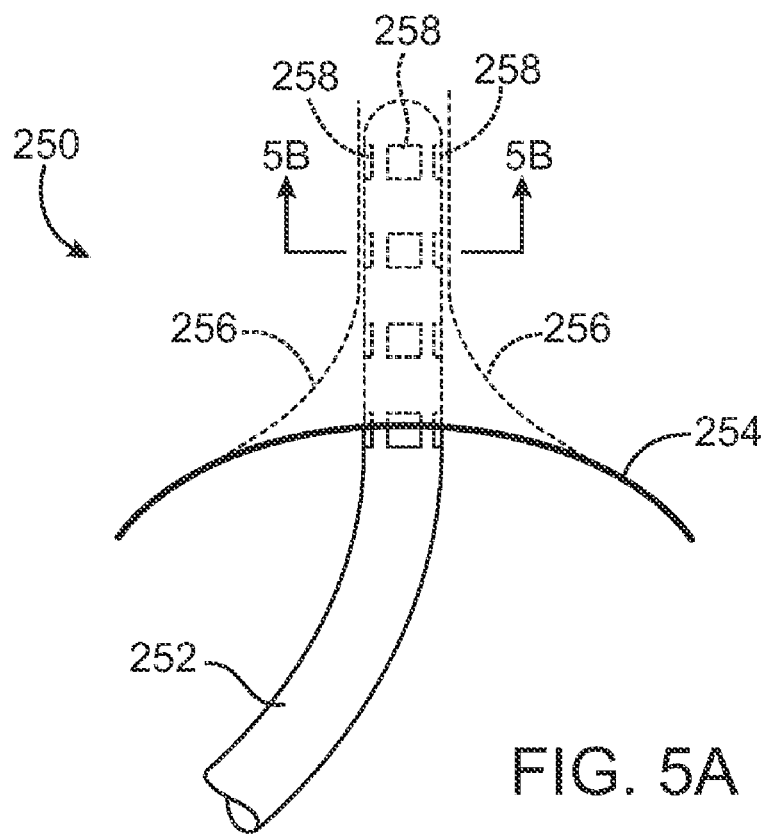
FIGS. 5A-5E show several variations of a closure device with collapsible electrodes.
Figure 5B:
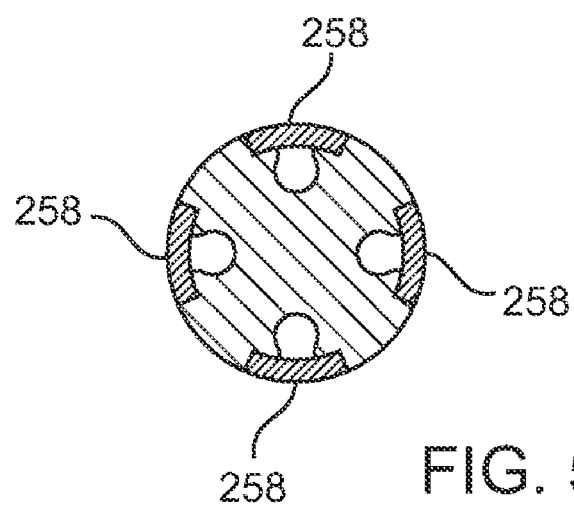
Figure 5C:
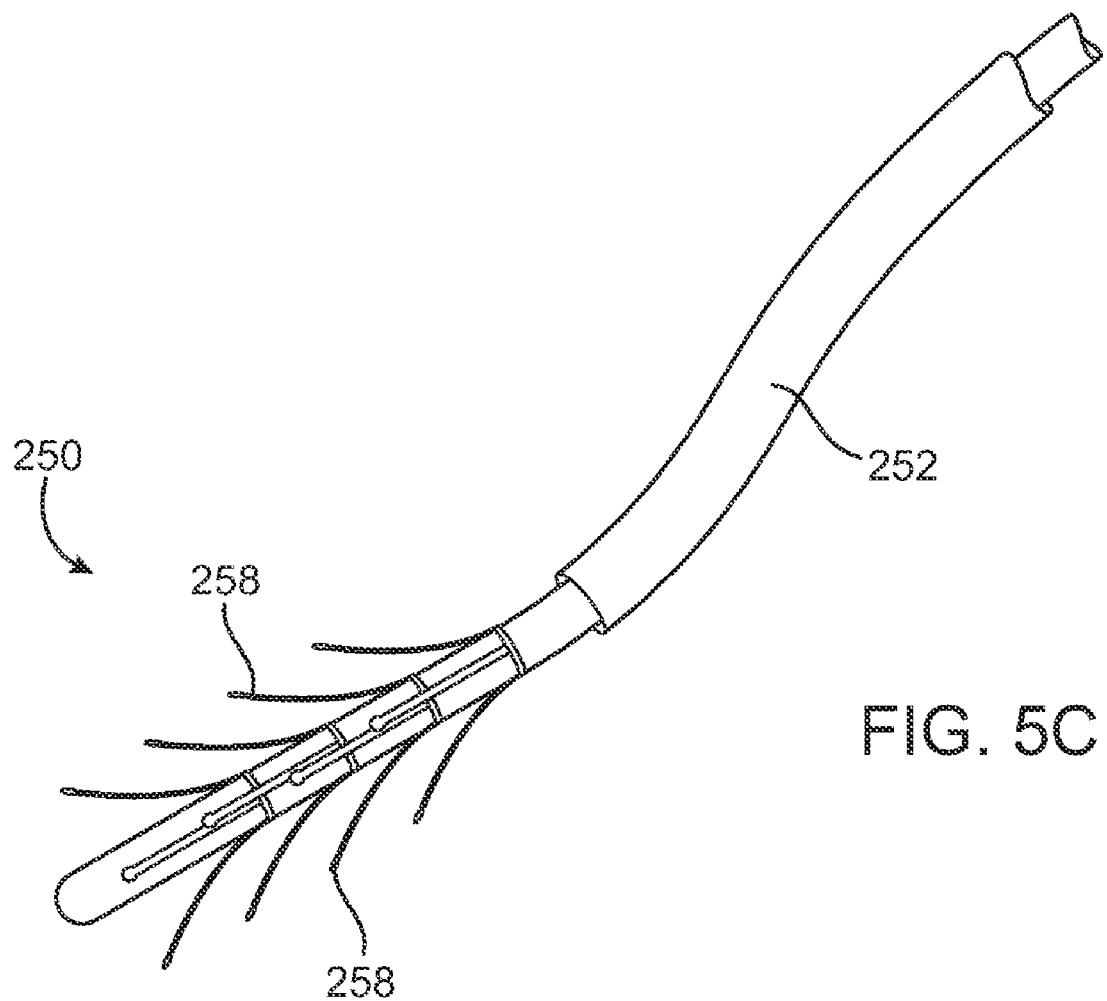

In another embodiment, collapsible electrodes 258 are employed on a closure device 250. FIGS. 5A-5C show closure device 250 with an elongated flexible catheter shaft 252 inserted into the mouth of a PFO 254 and into the PFO tunnel 256. Elongated flexible electrodes 258 protrude radially outward from the distal end of catheter shaft 252. Energy is delivered from the closure device 250 via electrodes 258 to the tissue defect. As the layered tissue defect closes around the electrodes 258, the flexible electrodes 258 collapse inwardly to allow the tunnel to substantially close. At the same time, catheter 252 is retracted out of and away from the PFO tunnel until the device 250 has been removed from the PFO defect. FIG. 5B illustrates a cross-section taken along line 5B-5B (FIG. 5A), at the distal end of closure device 250 and shows the electrodes 258 in a fully collapsed state. FIG. 5C is a perspective view of the closure device 250 of FIG. 5A.

Figure 5D:
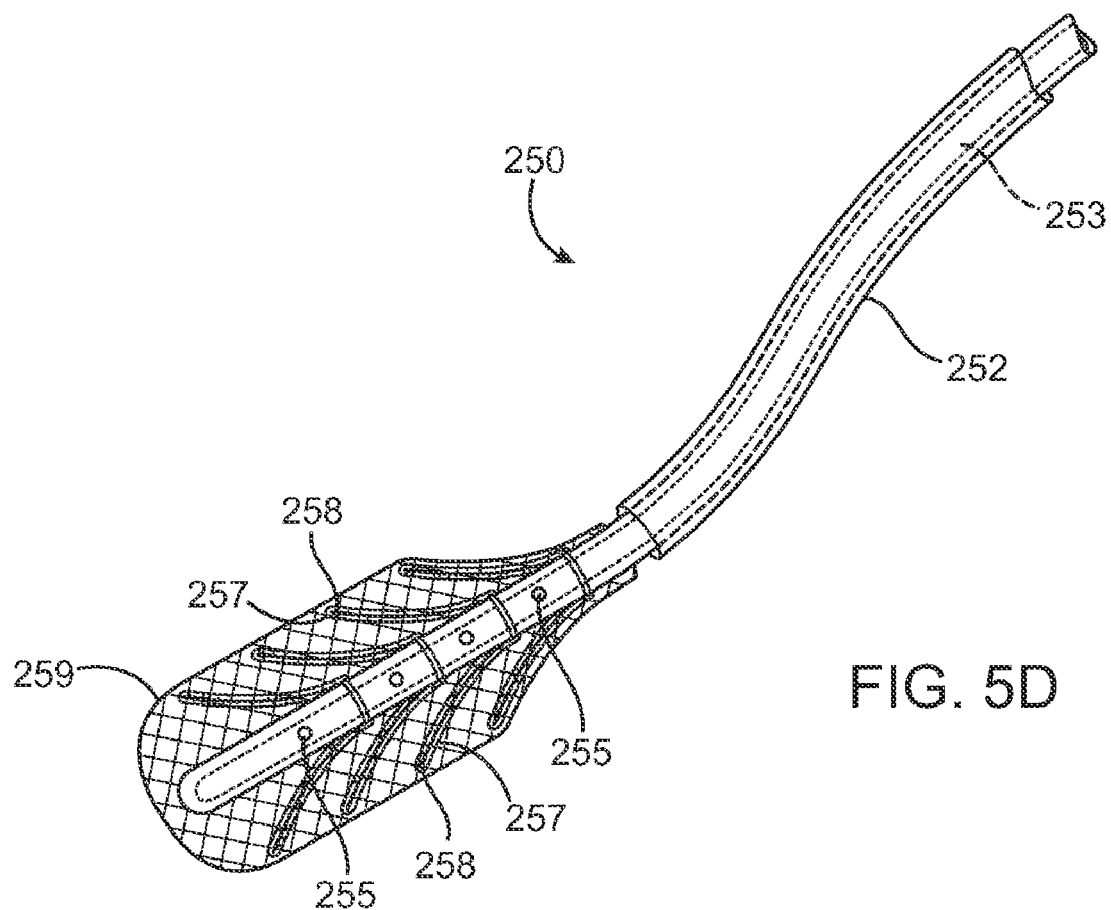
Figure 5E:
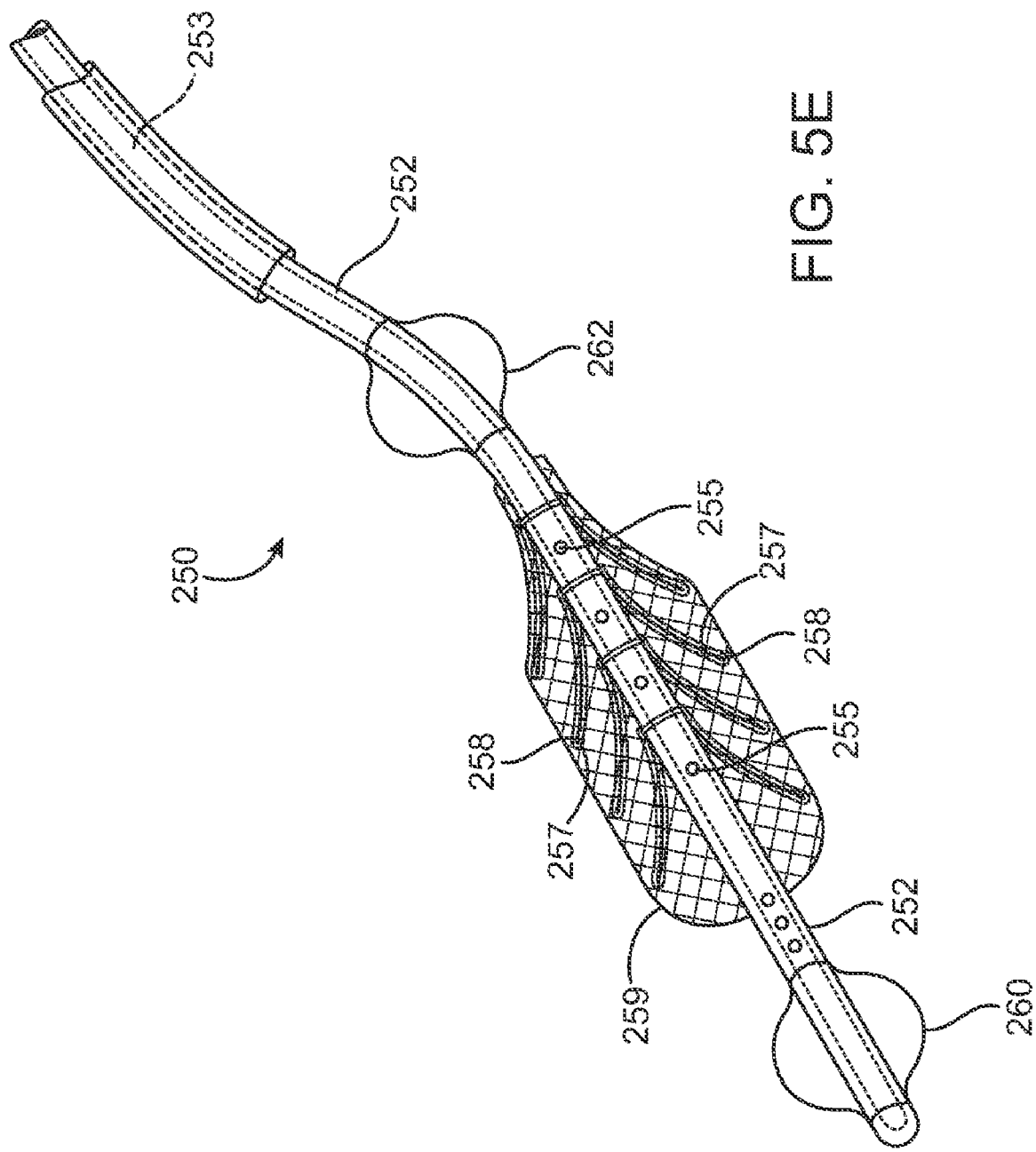

In this embodiment as well as others, the closure device 250 may further include a sock like covering 259 over the collapsible electrodes 258, as illustrated in FIG. 5D. The sock 259 may be formed of an implantable material such as collagen and may be used to facilitate closure of the layered tissue defect. The sock 259 may also comprise a lubricious inner liner 257 that is adapted to facilitate separation of the sock 259 from the collapsible electrodes 258. The closure device 250 may further allow delivery of collagen to the layered tissue defect with or without a cross-linking agent such as glutaraldehyde. These materials may be delivered to the tissue defect via a lumen 253 in the closure device 250 with distal apertures 255 on the closure device 250. Some embodiments may include an isolation system such that delivery of the cross-linking agent is restricted to a small region. FIG. 5E shows one such embodiment where balloons 260, 262 are placed proximal and distal to the sock 259. Balloons 260, 262 are expanded to a diameter sufficient to prevent the cross-linking agent from flowing past either balloon 260, 262, thereby limiting the cross-linking agent to the region therebetween.

Apparatus and methods according to the present invention may rely on energy, in various forms, to seal the PFO, either with or without an associated implant. Implants, such as patches, self-closing elements, or the like, may be welded into place using energy in a variety of ways. In various embodiments, any suitable type or configuration of welding substance, matrix, patch or the like may be used to enhance application of energy for providing PFO closure. Devices and methods using various types of energy and tissue welding substances to close PFOs are described fully in U.S. patent application Ser. No. 10/665,974, which was previously incorporated by reference.

Figure 6A:
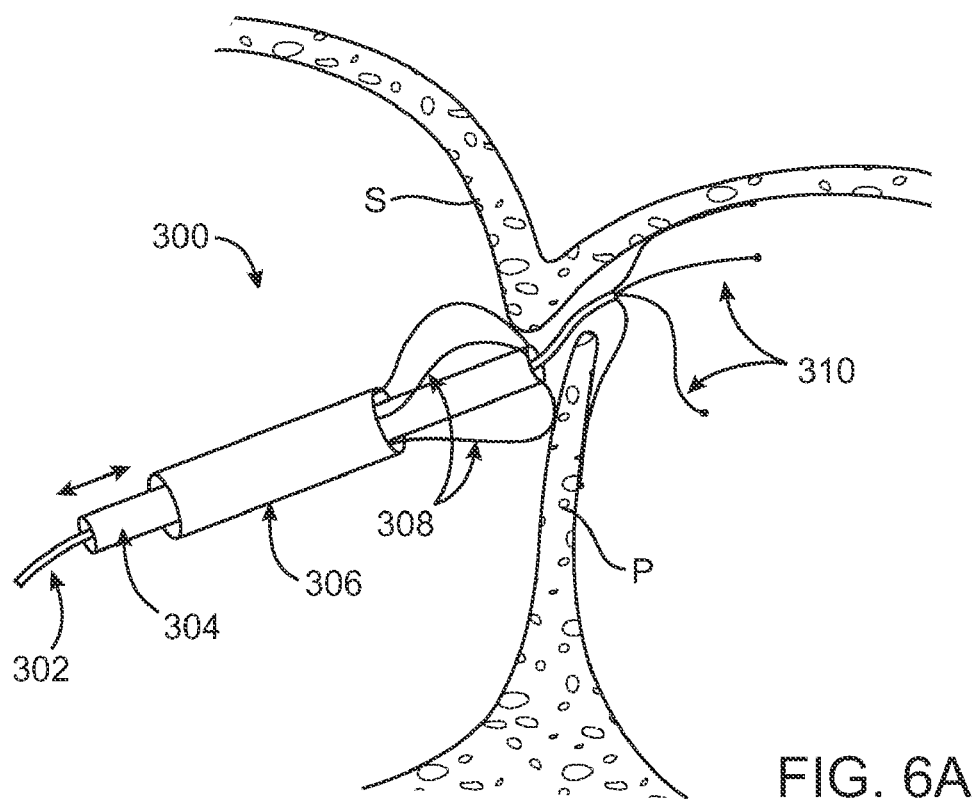
FIGS. 6A-6C depict a closure device with flexible members on the distal tip and a backstop element.
Figure 6B:
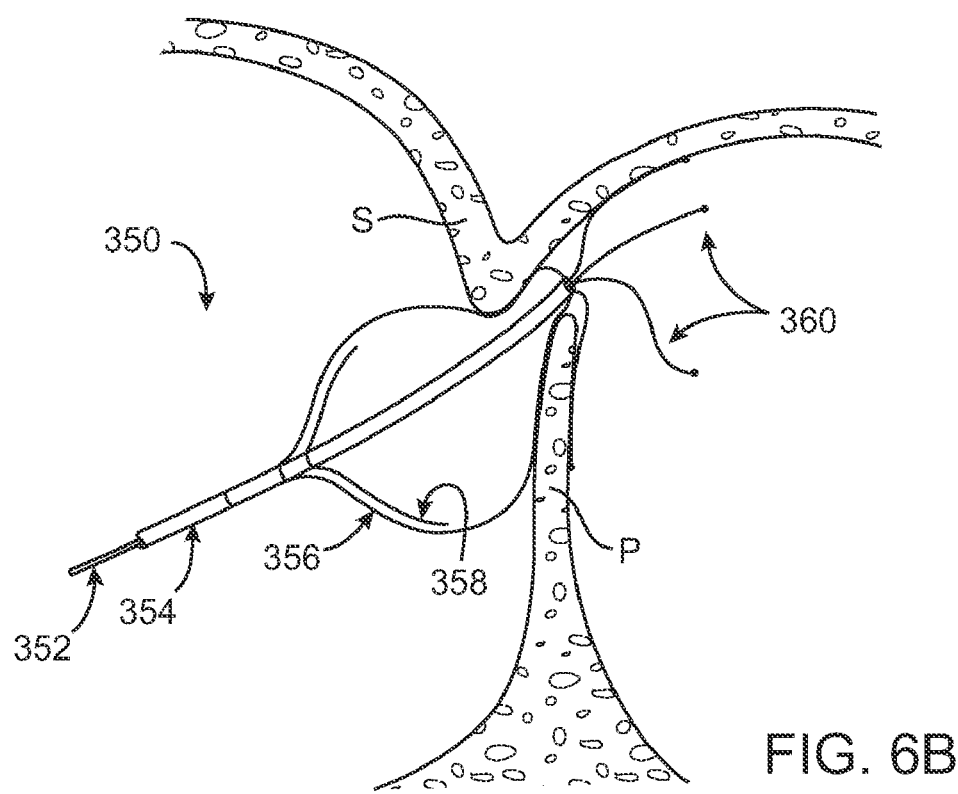

As an alternative to the implant-based devices, systems according to the present invention can function to weld the PFO closed with no implant left behind. As illustrated in FIGS. 6A-6B, in some embodiments, a backstop and energy delivery catheter are placed in contact with the PFO, and energy is delivered to disrupt the collagen matrix of the septum primum and septum secundum to cause fusion of the two parts of the PFO. Energy used can be monopolar RF (in which case the backstop acts as energy return, or ground electrode), or combinations thereof, ultrasound, laser, microwave, or resistance heating. Protein solder may be introduced to facilitate the weld.

Figure 6C:
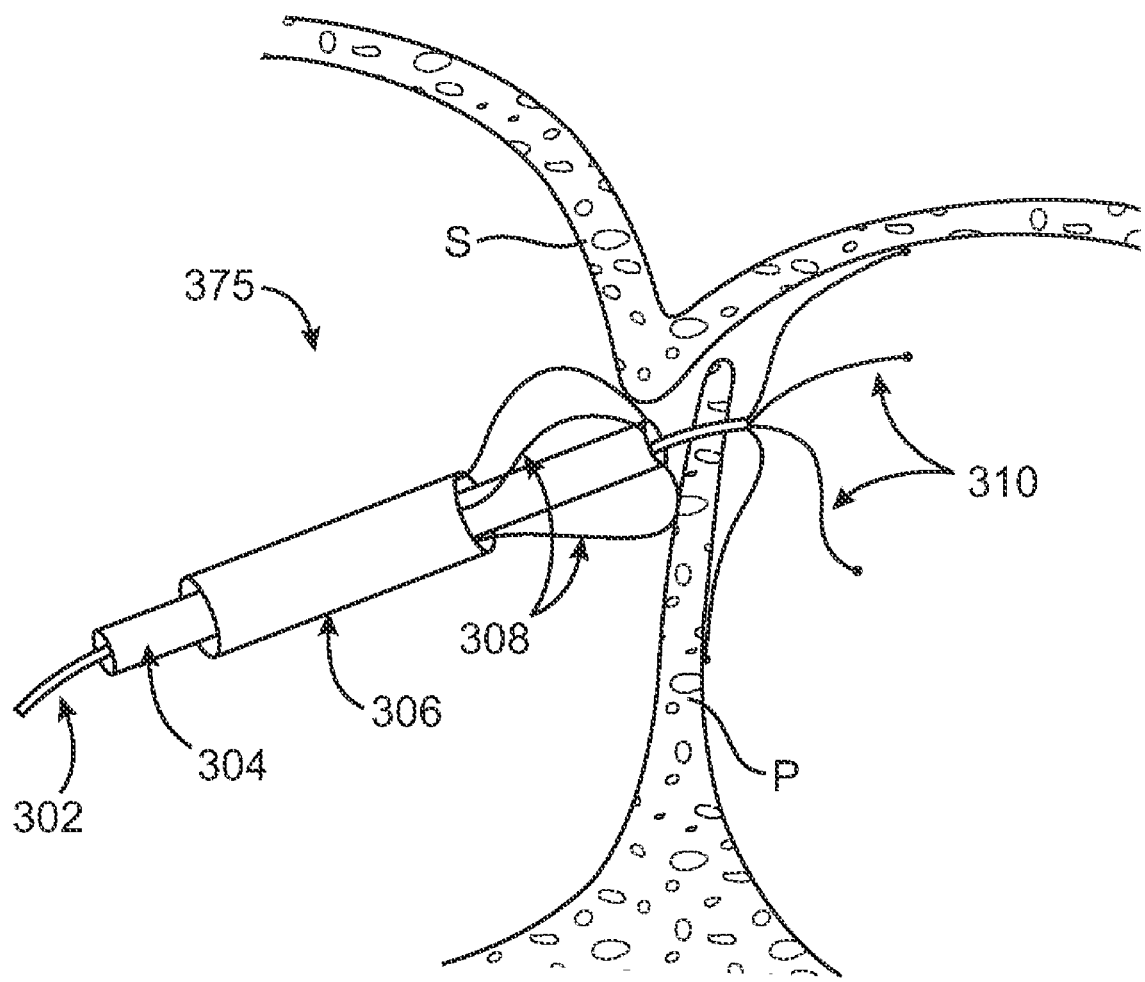

Referring to FIG. 6A, one embodiment of a catheter device 300 for treating a PFO (the opening between the septum primum P and septum secundum S) may include an outer catheter shaft 306, an inner catheter shaft 304 slidably disposed within outer shaft 306, a backstop 310 coupled with a backstop actuator 302 extending through inner shaft 304, and energy delivery members 308. Energy delivery members 308 may deliver any suitable form of energy for providing PFO closure, such as but not limited to RF, ultrasound, laser or microwave energy. In some embodiments, backstop 310 may act as an energy return member, such as when bipolar RF energy is used. As with other embodiments, the energy delivery members 308 are flexible. They are inserted into the layered tissue defect and then retracted as energy is applied to the defect. The backstop 310 ensures that layers of the tissue defect are well apposed and thus the delivered energy can effectively seal the PFO tunnel. This embodiment may also be used transeptally as shown in FIG. 6C. In FIG. 6C, catheter device 375 is used in a similar fashion as described above with respect to FIG. 6A, except that backstop 310 is inserted through the septum into the left side of the heart in order to ensure that tissue layers are apposed with one another and with energy delivery members 308.

As illustrated in FIG. 6B, an alternative embodiment of a catheter device 350 may include a catheter shaft 354, an expandable member 356, an energy delivery member 358 disposed within expandable member 356, and a backstop 360 coupled proximally with an actuator 352. Expandable member 356 and backstop 360 are used to position catheter device 350 in a desired location for treating the PFO, and energy is then applied via energy delivery member 358. In one embodiment, for example, energy delivery member 358 may comprise an ultrasonic piezo-foil, though any other suitable delivery device may be used in alternate embodiments.

Figure 7A:
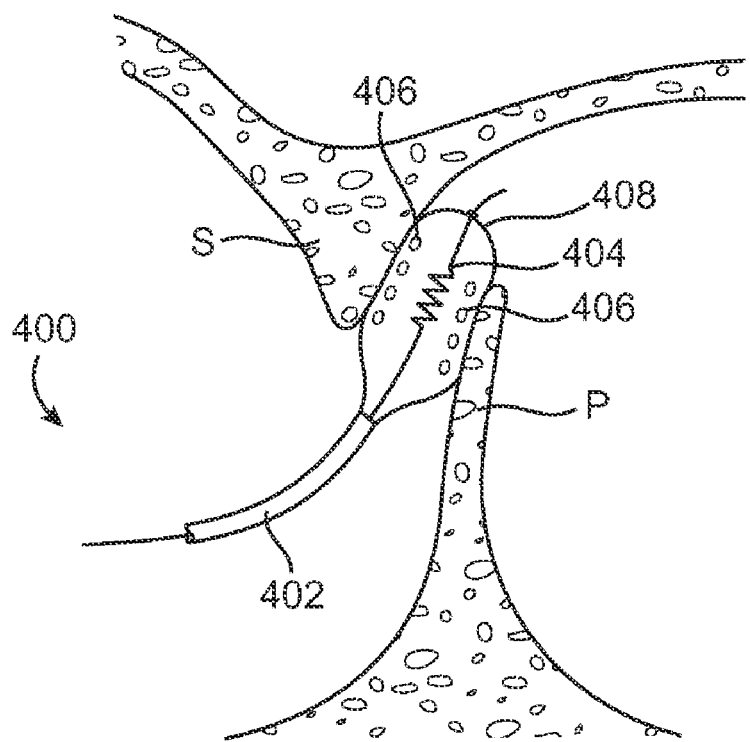
FIGS. 7A-7E illustrate several embodiments of a closure device utilizing a balloon to close a layered tissue defect.

Referring to FIG. 7A, an alternative embodiment of a catheter device 400 for treating a PFO includes a catheter body 402, an expandable member 408 having apertures 406 for allowing passage of fluid and an energy transmission member 404. In this embodiment, the force applied by expanding expandable member 408 may be sufficient to appose tissues, or a proximally directed force may be applied to expandable member 408, such as by pulling back on catheter body 402, to bring the tissues together.

Figure 7B:
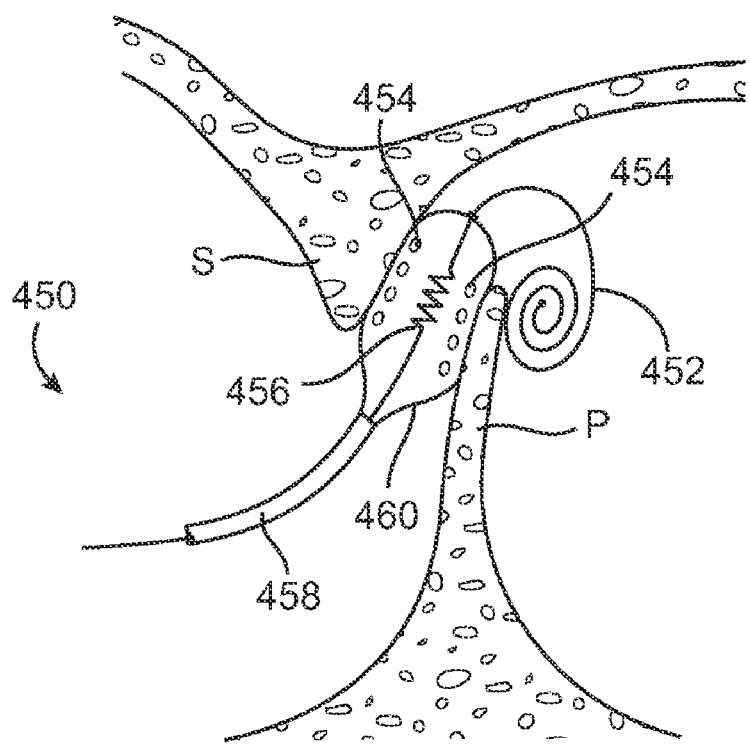

Referring now to FIG. 7B, one embodiment of a catheter device 450 includes a catheter body 458, an expandable member 460 having an energy transmission member 456 disposed within it and apertures 454 on its surface for allowing passage of conductive fluid, and a shaped distal portion 452. Shaped distal portion 452 resides in the left atrium and acts as a surface or "backstop," such that tissue may be brought together between shaped distal portion 452 and expandable member 460. In the embodiment shown, shaped portion 452 is a helical coil, which may be made of shape memory material, spring stainless steel or the like, so that it has a relatively straight configuration while disposed within catheter body 458, but assumes the coiled configuration when released. In other embodiments, other backstop devices may be used, such as those described more fully in U.S. patent application Ser. No. 11/472,923 and U.S. Provisional Patent Application No. 60/478,035, the contents of which are hereby incorporated by reference.

Figure 7C:
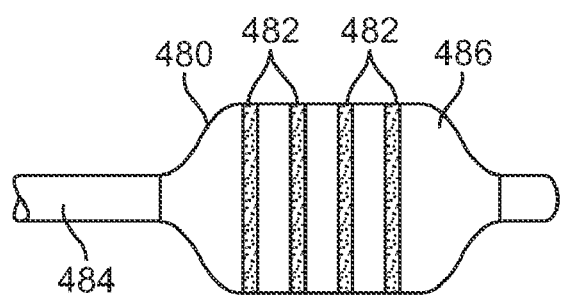
Figure 7D:
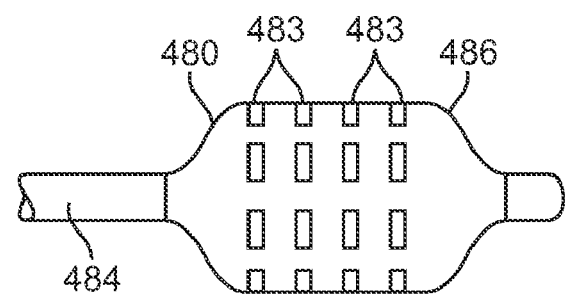
Figure 7E:
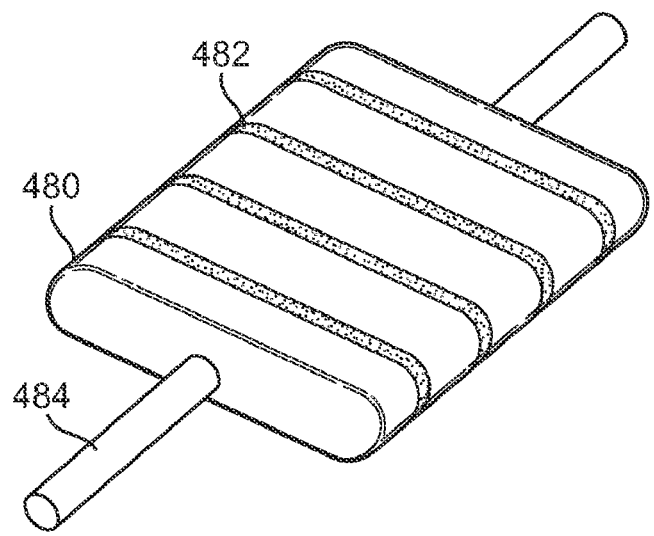

In an alternative embodiment, FIG. 7C shows how the expandable member 408 and 460 in FIGS. 7A and 7B respectively, may comprise energy transmission members 482 on the surface 486 of the expandable member 480. In FIG. 7C, the expandable member is a balloon 480. The balloon 480 is mounted on the distal end of a catheter 484. Here, the energy transmission members 482 are electrodes circumferentially disposed around balloon 480. The electrodes also could be disposed axially or in other patterns such as a winding helical shape. Alternatively, as shown in FIG. 7D, segmented energy transmission members 483 such as electrodes may be disposed on the balloon surface 486 in order to more precisely control how energy is delivered to the treatment region. In use, the balloon member 480 may be placed within the tunnel of the PFO in its deflated state, inflated, energized, and as energy is being applied, deflated to allow the tissues of the PFO to contact one another as the balloon device is removed. In order to facilitate closure of the PFO and bring the PFO tissues together while energy is being applied to close the PFO, the balloon can be deflated to reduce the surface area in contact with the tissue to allow the tissues of the PFO to contact one another and form a tissue bond. Additionally, it may be desirable to pull the balloon device proximally during or after deflation to assist in bonding of the tissue. The balloon 480 may be formed from a variety of materials, including compliant as well as non-compliant materials. FIG. 7E shows a flat balloon 480 that is rectangular in shape and adapted to fit into a PFO tunnel. When expanded, the balloon exerts a lateral force against the tissues of the PFO thereby bringing the tissues together.

Figure 8A:
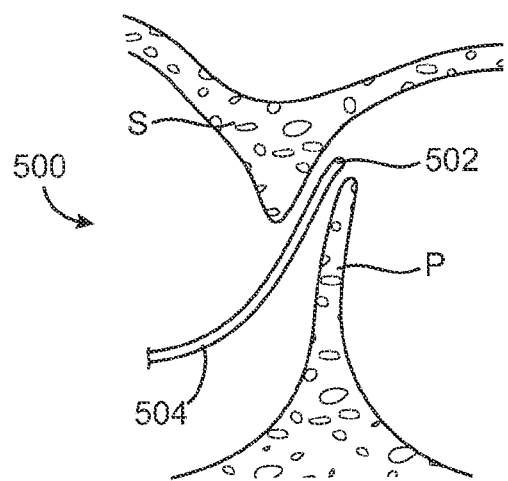
FIGS. 8A-8D show how one or more catheters or guide wires may be used to close a layered tissue defect.

FIGS. 8A-8D illustrate embodiments where a simple elongate flexible member 504, 554 and 586, such as a guide wire is placed in between the primum P and secundum S layers of tissue in a PFO. The guide wire 504 may be adapted to serve as an energy transmission member. For example, energy can be delivered into the PFO tunnel as the guide wire is retracted, thus energizing the effective region of the PFO tunnel and closing it. In FIG. 8A, a closure device 500 comprises an elongate flexible member such as a guide wire 504. The distal end 502 is inserted into the PFO tunnel so as to deliver energy to the tunnel. The guide wire is easily retracted through the PFO tunnel as energy is applied to the defect. Additionally, the guide wire may be moved back and forth around the defect as well as and in and out of the tissue defect so as to deliver energy to a wider area of the defect.

Figure 8B:
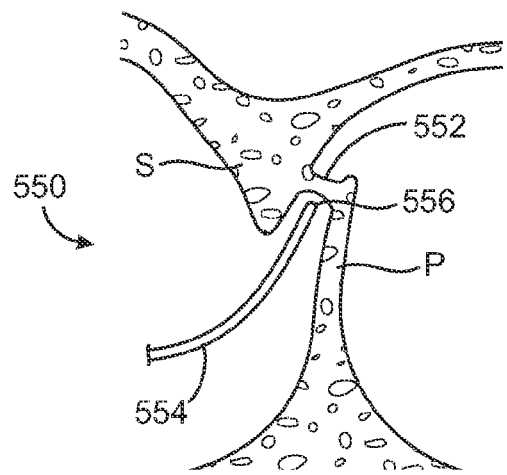

In FIG. 8B, the closure device 550 comprises an elongate flexible member such as a guide wire or catheter 554. The closure device 550 is inserted into the PFO tunnel formed by the primum P and secundum S and the distal end 556 delivers energy to the tunnel. In this embodiment, only the distal end 552 of the tunnel is sealed and then the closure device 550 is removed. By sealing the distal end 552 of the PFO tunnel, it is believed that the healing process at the distal location will be sufficient to close the defect, or in some cases, if not sufficient due to the size of the PFO, the healing process will propagate the closure along a majority of the tunnel length.

Figure 8C:
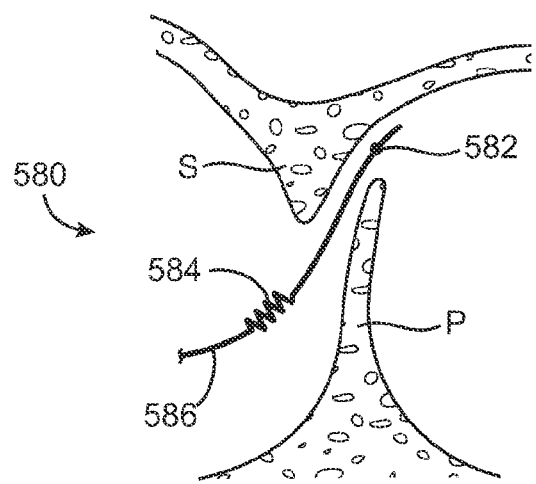
Figure 8D:
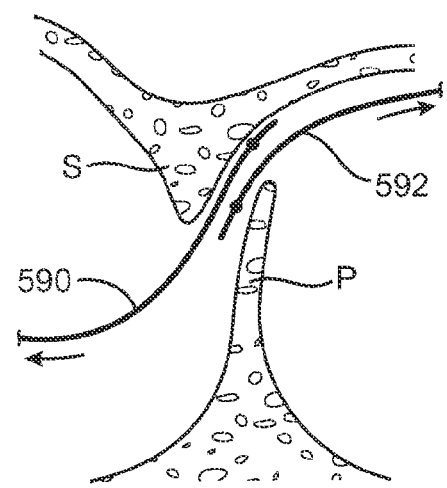

FIG. 8C shows a variation on the embodiments of FIGS. 8A and 8B. Here, a variable resistor 584 is placed in line with the guide wire 586. The variable resistor 584 allows an operator to adjust the energy delivered by closure device 580 to the PFO tunnel. An electrode 582 disposed on the guide wire 586 directs energy to the layers of tissue in the PFO. In alternative embodiments, dual guide wires may be used to seal the PFO tunnel. In these embodiments, one guide wire 590 is placed in the PFO tunnel from one side of the heart while a second guide wire 592 is placed in the PFO tunnel from an opposite side of the heart. Energy is delivered to the PFO simultaneously by both guide wires as they are retraced in opposite directions. This is illustrated in FIG. 8D.

FIG. 19 shows an alternative embodiment of a guide wire energy transmission member. In FIG. 19, closure device 1900 comprises an elongated, flexible guide wire 1906 axially disposed in a sheath 1902. The guide wire 1906 is insulated 1904 along its length with the distal portion 1908 remaining uninsulated so that energy may be delivered from the tip 1908. The guide wire 1906 may be retracted into the sheath 1902 during delivery and then advanced into the tissue defect during the therapeutic delivery of energy. An axially disposed member 1910 may provide a conductive pathway from the uninsulated tip 1908 back to the proximal end of the closure device 1900. Additionally, the axially disposed member 1910 may also be used to deploy and retract the guide wire 1906 from the sheath 1902. Alternatively, guide wire 1906 may be pre-shaped to form various patterns such as sinusoidal or zig-zag configurations upon deployment from the sheath. In operation, these embodiments may allow the energized portion to effect a greater surface area within the tunnel of the PFO.

Figure 9A:
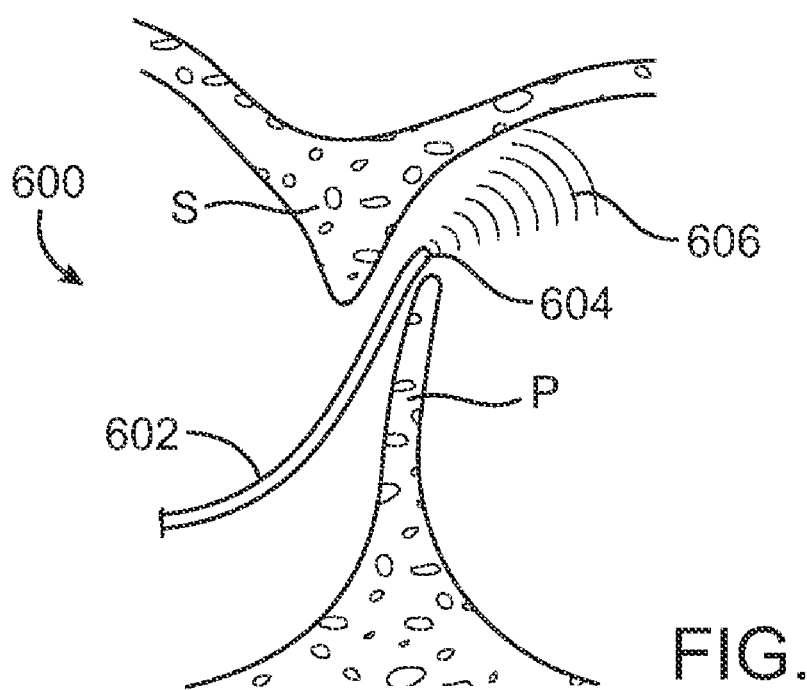
FIGS. 9A-9B show how intravascular ultrasound is used to image the layered tissue defect.
Figure 9B:
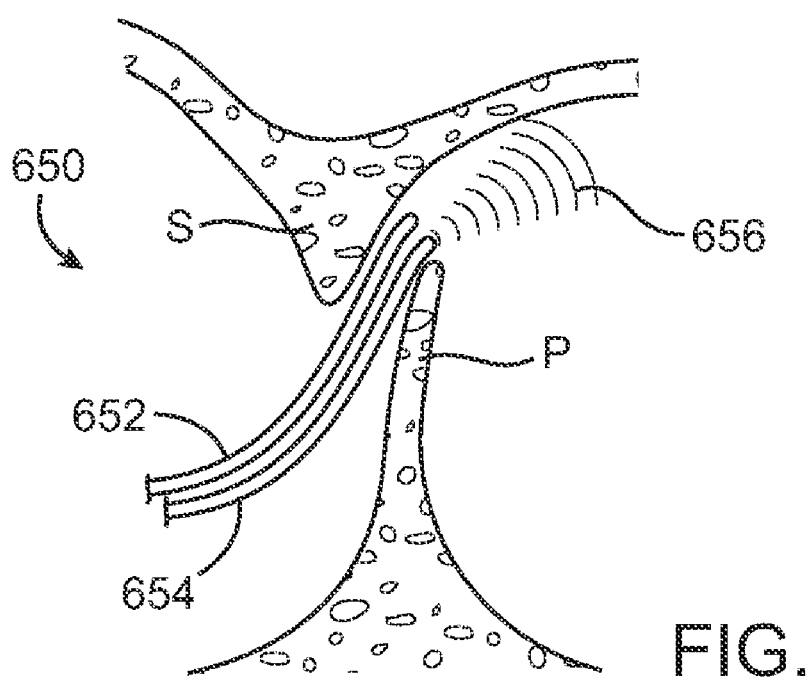

FIGS. 9A and 9B illustrate how intravascular ultrasound (IVUS) or intracardiac echocardiography (ICE) may be employed in the PFO tunnel closure procedure. IVUS or ICE may be used to image the PFO as an aid in determining the effectiveness of the closure treatment. IVUS and ICE methods and apparatus are well known in the art and many references may be found in the medical and patent literature. Exemplary products currently commercially available include the Atlantis® SR Pro coronary imaging catheter and Galaxy²™ IVUS imaging system available from Boston Scientific Corporation (Natick, Mass.), as well as Eagle Eye™ Gold, Visions™ PV018 and Revolution™ IVUS catheters manufactured by Volcano Corporation (Rancho Cordova, CA).

In FIG. 9A, the closure device 600 comprises a closure catheter 602 adapted to deliver energy to the PFO as well as an IVUS member 604 that can image the PFO tunnel 606. In this embodiment, the IVUS member 604 is integral with the closure catheter 602. However, in FIG. 9B, closure system 650 has an IVUS member 654 separate from the closure catheter 652. In this embodiment, the IVUS member 654 is alongside the closure catheter 652 and the IVUS member can image the PFO tunnel with ultrasound 656 before, during and after the closure procedure. Other imagining modalities may also be employed such as fluoroscopy.

Additionally, ultrasound markers may be placed on the closure device in order to enhance device visibility under ultrasound. For example, FIG. 26 illustrates a bottom view of a closure device 2600. The closure device 2600 comprises a housing 2604 that can appose tissues of the PFO and a central lumen 2602 exits the housing 2604 near its center. The central lumen may be used to accommodate a guide wire and/or a vacuum. Electrodes 2606 on the bottom of the housing 2604 allow energy to be transferred to or from the tissues of the PFO. Ultrasound markers 2608 placed on the housing 2604 help a physician to observe the closure device under ultrasound.

FIG. 27 illustrates how an ultrasound transducer may be incorporated into a closure device. Incorporating ultrasound allows visualization of device position and thus helps to ensure that the closure device is properly seated against the PFO which in turn helps assure that an effective closure treatment is applied to the PFO. Current fluoroscopy and intracardiac echocardiography tools do not always provide adequate resolution to visualize a PFO. In FIG. 27, closure device 2700 comprises a housing 2702 coupled to a catheter shaft 2706. A two-dimensional ultrasound transducer 2708 is also disposed in the distal portion of the housing 2702. Ultrasound transducers 2708 may include phased array as well as rotational transducers. Other elements of the closure device such as a central lumen 2602 and energy transmission member 2606, as illustrated in FIG. 26 may be included in the closure device 2700. The horizontal sweep 2704 of the ultrasound transducer 2708 is shown. A PFO tunnel as observed under ultrasound would appear as depicted in FIG. 28. The tunnel 2806 of a PFO 2800 is seen formed between tissue layers 2802 and 2804. Additionally, the ultrasound device may be used to visualize guide wire position during initial placement. In FIG. 29, a guide wire 2902 is placed in the tunnel 2912 of a PFO, in between tissue layers 2908 and 2910. A closure device 2904 with ultrasound imaging capability is advanced over the guide wire. Ultrasound 2906 is then used to visualize the position of the guide wire 2902 within the PFO tunnel 2912. Similarly, in FIGS. 30A and 30B, ultrasound is used to visualize the tunnel as it is sealed. In FIG. 30A, the closure device 3002 with ultrasound capability scans 3004 across the tissue defect to provide an image of a patent PFO tunnel 3010 between tissue layers 3006, 3008. Imaging may be conducted during the closure treatment and in FIG. 30B, an image of the closed PFO tunnel 3012 after treatment is seen.

In addition to a closure device with ultrasound capability of imaging into a PFO, an ultrasound device 3110 may be placed into the PFO tunnel 3108 to image back into the right side of the heart, as shown in FIGS. 31A-31B. In FIG. 31A, an ultrasound device 3110 is either incorporated as a part of a guide wire 3102 or the ultrasound device 3110 is advanced over a guide wire 3102 into the PFO tunnel 3108, in between tissue layers 3104 and 3106. The ultrasound probe images away from the PFO tunnel 3108, toward the right side of the heart 3112 as seen in FIG. 31B. This allows the user to see a closure device 3114 coupled with a catheter shaft 3116 as the closure device 3114 is advanced over guide wire 3102 into apposition with the PFO. As previously described, ultrasound markers may be incorporated into the closure device to enhance visualization under ultrasound, as shown in FIG. 26 above. In some embodiments, the closure device automatically signals a user when the markers are detected, thereby providing an indication that the closure device is properly positioned relative to the PFO tunnel.

Figure 10A:
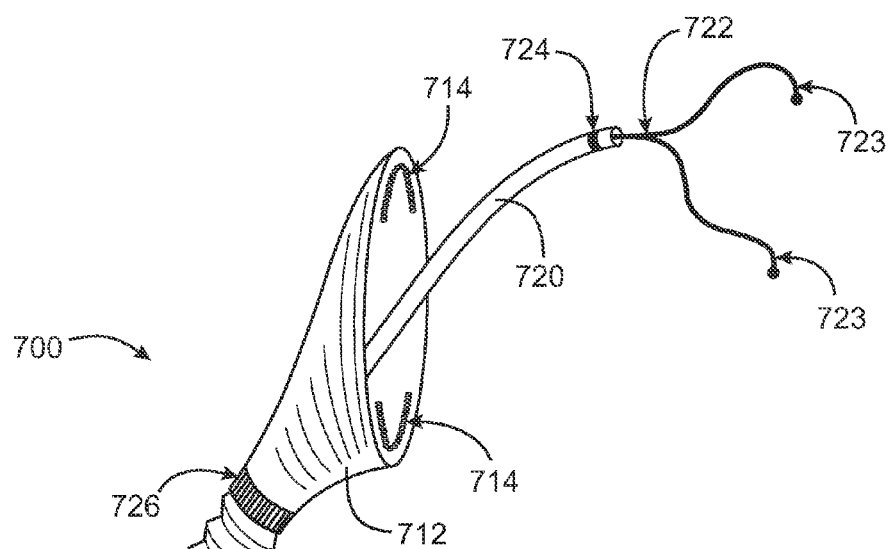
FIG. 10A-10C show another embodiment of the layered tissue closure device.
Figure 10B:
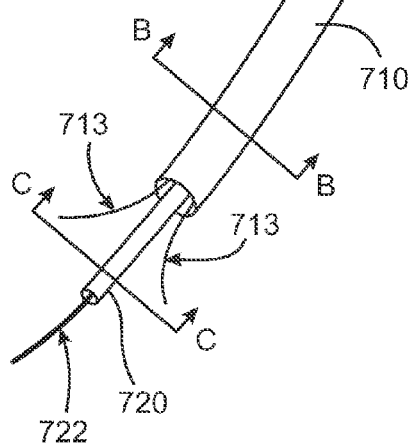
Figure 10B:
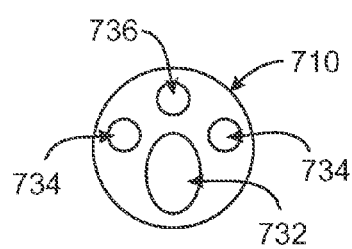
Figure 10C:
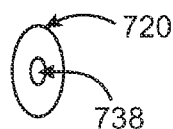

Referring now to FIGS. 10A-10C, one embodiment of a PFO treatment apparatus 700 suitably includes a catheter device 710 coupled with a tissue apposition member 712 at its distal end. One or more energy transmission members 714 may be disposed through or within catheter device 710 and/or coupled with tissue apposition member 712. Conductor wires 713 couple energy transmission members 714 with the proximal end of the catheter device 710. In some embodiments, catheter device 710 is slidably disposed over a guide catheter 720. Guide catheter 720 may contain one or more expandable elements 722, such as a guide wire or the like. In some embodiments, expandable elements 722 having distal tips 723 may also serve as energy transmission members. One or more radiopaque markers 724, 726 may be included on catheter device 710, guide catheter 720 or both. Catheter device 710 may also include an isolation portion 728. Tissue apposition member 712 is isolated from catheter device 710 by the isolation portion 728, and this helps stabilize tissue apposition member 712 from movement of catheter device 710, which prevents tissue apposition member 712 from losing its position.

FIGS. 10B and 10C show cross-sectional views of apparatus 700 from the perspective of lines B-B and C-C in FIG. 10A, respectively. In FIG. 10B, catheter device 710 is shown, having a guide catheter lumen 732, two energy transmission member lumens 734 and a vacuum lumen 736. As shown in FIG. 10C, guide catheter 720 includes an expandable element lumen 738. Guide catheter lumen 732 may sometimes be configured with an inner diameter (or "profile") that is shaped (or "keyed") to allow guide catheter 720 to pass easily through lumen 732. This feature is demonstrated in FIGS. 10B and 10C, where guide catheter 720 and guide catheter lumen 732 each have an ovoid shape.

In general, catheter device 710 includes an elongate, flexible catheter which may be advanced through the vasculature of a patient to a position in the heart for treating a PFO. Thus, catheter device 710 may have any suitable length, diameter, cross-sectional profile and the like, and may be constructed of any suitable material. Tissue apposition member 712 (or multiple tissue apposition members in some embodiments) is disposed at or near the distal end of catheter device 710. Although many different types of devices may be used to bring tissues of the PFO together, in one embodiment tissue apposition member 712 is also adapted to cover the PFO. Tissue apposition member 712 may be positioned to contact adjacent PFO tissues to fully cover, or block, the opening of the PFO. This blocking of the PFO may prevent right-to-left shunting of blood and may allow blood pressure in the left atrium to bring the septum primum and septum secundum at least partially together to close the PFO. Therefore, tissue apposition member 712 may help bring the PFO tissues together to assist in PFO closure simply by forming a seal or blockage over the PFO.

In this and other embodiments, tissue apposition member 712 may also include one or more vacuum members for applying vacuum to the PFO tissues. In one embodiment, for example, suction lumen 736 (FIG. 10B) may extend from the proximal end to the distal end of catheter device 710, opening into one or more vacuum-application apertures at the distal end of tissue apposition member 712. The vacuum-application aperture(s) may have any suitable configuration, such as a continuous aperture encircling tissue apposition member 712, multiple apertures encircling tissue apposition member 712 or in any other suitable configuration at or near its distal end, or the like. In still another embodiment, vacuum may be applied via a large, central lumen in tissue apposition member 712. In any case, vacuum force may be used to bring PFO tissues together and/or to secure tissue apposition member 712 and thus catheter device 710 to the PFO tissues.

Tissue apposition member 712, especially when configured as a PFO-covering member, may be collapsible/expandable to facilitate advancement and delivery of catheter device 710. For example, tissue apposition member 712 may comprise a collapsible polymeric cover disposed over an expandable/collapsible frame. In other embodiments, tissue apposition member 712 may be constructed of a shape memory material, such as NiTi or another shape memory metal, spring stainless steel or the like, to allow catheter device 710 to be delivered through vasculature and then allow tissue apposition member 712 to expand to contact and appose the PFO tissues. In some embodiments, catheter device 710 and tissue apposition member 712 may be delivered to a location for PFO treatment through an introducer sheath. To further enhance the use of apparatus 700, an angle between catheter device 710 and tissue apposition member 712 may be selected to approximate a convenient angle for delivery and/or deployment. In one embodiment, for example, the angle between catheter device 710 and tissue apposition member 712 may approximate the angle between the inferior vena cava and the interatrial septum. Any other configuration, combination of angles and the like is contemplated, however. In some embodiments, for example, direct steering of the angle of tissue apposition member 712 relative to catheter device 710 may be employed to enhance delivery of catheter device 710 to a treatment site.

To further facilitate use of apparatus 700, catheter device 710 may include one or more radiopaque markers 726 for facilitating visualization of the device 710. Catheter device 710 may also include a flexible isolation portion 728, which in some embodiments comprises a rigid but shapeable portion disposed toward the distal end of catheter device 710, between tissue apposition member 712 and the generally flexible proximal portion of catheter device 710. Flexible isolation portion 728 may help to isolate tissue apposition member 712 from some or all movement experienced by the more flexible, proximal portion of catheter device 710, thus allowing a PFO treatment procedure to be performed without significant movement of tissue apposition member 712. In other embodiments, flexible isolation portion 728 may be more flexible than the more proximal portion of catheter device 710, thus enhancing maneuverability, shapability or the like of the position of tissue apposition member 712 relative to the more proximal portion.

Energy transmission members 714 may comprise any of a number of devices and may transmit any suitable type of energy for closing a PFO. Some types of energy which may be used, for example, include radiofrequency, cryogenic, resistive heat, direct heat, ultrasound, microwave and laser. Radiofrequency energy transmission members 714 may be either monopolar or bipolar or combinations thereof, with monopolar catheter devices also including a grounding member. Energy transmission members 714 may have any suitable configuration. For example, they may have a curved shape to approximate a radius of curvature of the PFO, as shown in FIG. 10A, which may be swept along the layered tissue defect. Also, as mentioned above, in some embodiments expandable elements 722 having distal tips 723 also serve as energy transmission members and they may be configured for welding specific regions of the PFO tissues from within the tunnel or welding around the circumference of PFO tissues. In some embodiments, energy transmission members 714 are fixedly coupled with tissue apposition member 712, while in other embodiments energy transmission members 714 are movable within tissue apposition member, for example to move about the circumference of the PFO to weld PFO tissues at multiple locations.

As mentioned earlier, the phrase "tissue welding" herein is used to mean application of energy to (or removal of energy from) PFO tissues to substantially and acutely close the PFO. Energy transmission members 714 generally provide for transfer of energy to or from PFO tissues to denature collagen in the tissues, and when the collagen is allowed to renature, with the tissues apposed, the once separated tissues bind together to form a stable tissue bridge. This stable tissue bridge substantially and acutely closes the PFO, preferably permanently. PFO tissues may, in some embodiments, be brought and held together by one or more tissue apposition members 712. Energy transmission members 714 provide sufficient energy transfer, for a sufficient time, to weld the tissues. The time span of energy transmission may be, for example, from about 0.5 seconds to about 15 minutes. Energy transmission, in some embodiments, may be from about 0.5 Watts to about 50 Watts, and more preferably from about 2 Watts to about 20 Watts. Any other suitable energy and timing combination may also be used. In one experimental example, a PFO in a section of pig heart tissue used ex-vivo in a flowing saline test fixture was closed by applying suction to appose the PFO tissues and applying RF energy at approximately 25 Watts for 7 minutes. RF energy application was then discontinued, but suction was continued for an additional time period to keep tissues in apposition while the tissue cooled, to allow collagen in the tissues to reorganize and bind together to form a stable tissue bridge. Other energy amounts, energy application times, tissue apposition times and the like are contemplated. U.S. patent application Ser. No. 11/472,924, filed on Jun. 21, 2006 discloses such parameters and is assigned to the assignee of the present invention, the full disclosure of which is incorporated herein by reference.

Although any type of energy may be transmitted by energy transmission members 714, some embodiments will make use of monopolar or bipolar radiofrequency (RF) energy, or combinations thereof. Devices may use monopolar radiofrequency energy, or heat, for example, wherein energy is applied simultaneously to all conductive elements, completing the circuit through an external ground pad affixed to the skin of the patient. Alternatively, bipolar energy may be applied to all conductive elements simultaneously, and the circuit completed through a ground element incorporated elsewhere on apparatus 700. Further embodiments may include applying bipolar energy between two or more energy transmission members 714, which are electrically isolated from one another within catheter device 710. Monopolar and bipolar energy delivery and combinations of monopolar and bipolar energy delivery, termed "multipolar" energy delivery are described in U.S. patent application Ser. No. 11,403,038 filed Apr. 11, 2006; Ser. No. 11/403,052 filed Apr. 11, 2006; Ser. No. 11/402,489 filed Apr. 11, 2006 and U.S. Provisional Application No. 60/869,049 filed Dec. 7, 2006, the entire Contents of which are incorporated herein by reference.

Control systems coupled with energy transmission members 714 or tissue apposition member 712, or otherwise disposed within apparatus 700, may sense an amount of energy delivered to PFO tissues and, optionally, may automatically stop energy delivery upon detecting a change in condition of energy delivery, for instance an increase in electrical resistance or impedance in PFO tissues or in apparatus 700, an increased energy draw from the treatment apparatus, or a sudden temperature rise, and/or the like. In some embodiments, energy delivery may be automatically stopped when an amount of delivered energy reaches a desired level, such as an amount of energy sufficient to substantially close the PFO. The amount of delivered energy may be monitored by any suitable method, such as monitoring temperature or impedance in PFO tissues or the like. In some embodiments, one or more sensors coupled with tissue apposition member 712, energy transmission members 714, or any other part of apparatus 700 may be used for monitoring such indicia. Examples of sensor devices include but are not limited to infrared sensing devices, thermistors and thermocouples. A control system may also include a microprocessor coupled with the sensors to determine when a desired amount of energy has been delivered and/or to automatically stop energy transmission. In alternative embodiments, a microprocessor may be included in apparatus 700 which can sense, monitor and control energy delivery, thus not requiring separate sensors.

With continued reference to FIG. 10A, some embodiments of apparatus 700 include guide member 720 which can include a guide catheter, guide wire or other guide, or an alternative guide member as discussed further below. Guide member 720 is generally a flexible catheter along which catheter device 710 may be slidably advanced to a position for PFO treatment. Guide catheter 710 is configured to fit at least partially within a PFO and optionally through a PFO into the left atrium of the heart. Optionally, one or more radiopaque markers 724 may be included on guide catheter.

Guide catheter 720 may contain one or more expandable members 722 or other similar devices for expanding within the PFO to help bring the PFO tissues together, anchor catheter device to the PFO tissues, or both. As shown in FIG. 10A, for example, a "fish mouth" or two-prong expandable member 722 may be deployed within a PFO. When the two arms of the fish mouth separate, PFO-adjacent tissues are stretched laterally such that they tend to come together in the middle. In some embodiments, expandable members 722 may assist in PFO tissue apposition either while extending into the left atrium, while in other embodiments expandable members 722 do not extend into the left atrium. Other embodiments for expanding within the PFO are discussed in U.S. patent application Ser. Nos. 11/403,038 and 11/464,755, the entire contents of which are hereby incorporated by reference.

Expandable member 722 may have any suitable configuration and may be constructed from any suitable materials. For example, expandable member 722 may be spring loaded, made of shape memory material, such as nitinol or spring stainless steel or the like. Alternatively, expandable member 722 may be expanded mechanically by one or more expansion members coupled with expandable member 722 and controlled via an actuator at the proximal end of guide catheter 720. During delivery of guide catheter 720, expandable member 722 resides within guide catheter 720. Guide catheter 720 may then be withdrawn to deploy expandable member 722 either within the PFO or within the left atrium to be drawn back into the PFO. In some embodiments, expandable member 722 has one or more pre-shaped or shapeable distal tips 723. Tips 723 may be used, for example, to help locate and cross the PFO. Tips 723 may also be used to contact a left atrial surface of the septum primum or other PFO tissue, so that when the expandable member 722 is pulled proximally tips 723 help bring the PFO tissues together and/or anchor apparatus 700.

In some embodiments, one or more expandable members 722 may include or be coupled with one or more energy transmission members. For example, expandable member 722 may include one or more radiofrequency transmission members for monopolar or RF transmission, or combinations thereof. A fish mouth expandable member 722, for example, may include a bipolar RF transmission member on each prong of the fish mouth. In some embodiments, energy transmission members may be included in or coupled with both expandable member 722 and tissue apposition member 712. In any such embodiments, some portions of the energy transmission member(s) may be insulated, to prevent unwanted energy transmission to tissues. For example, in some embodiments a distal tip extending to contact a left atrial surface of PFO tissues may be insulated to prevent energy transmission from the tip.

FIGS. 11A-11E demonstrate a method for treating a PFO according to one embodiment of the present invention. It should be emphasized that this is merely one possible embodiment, and that many alternative methods are contemplated. For example, steps may be modified, repeated, added or deleted from the method, the order of steps may be changed, and/or the like, without departing from the scope of the invention as defined by the appended claims. Therefore, the foregoing description should not be interpreted to limit the scope of the invention in any way.

Figure 11B:
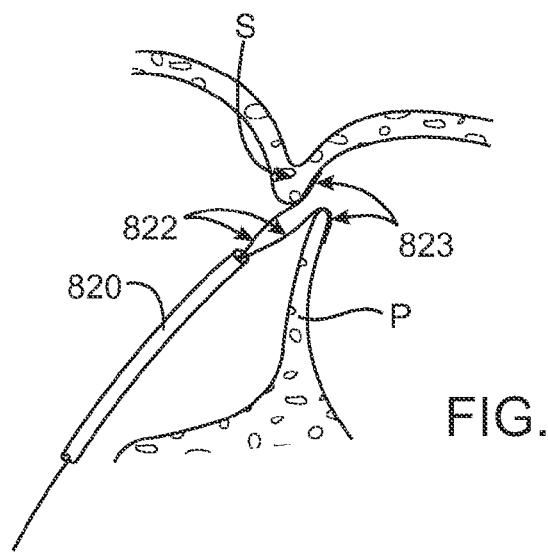

That being said, in one embodiment, a PFO treatment method includes advancing a guide member 820 through the PFO, between tissues P and S, adjacent to the PFO, the guide member 820 containing an expandable member, as depicted in FIG. 11A. Guide member 820 is then retracted (proximally pointing arrow) to expose expanding member 822. This is illustrated in FIG. 11B. Expanding member 822 may be exposed/expanded within the PFO, or may alternatively be exposed/expanded within the left atrium and pulled back into the tunnel of the PFO. Expanding member 822 may also include one or more distal tips 823, which may help to locate the PFO, cross the PFO, appose the tissues P, S and/or to anchor guide member 820 to the tissues P, S.

Figure 11C:
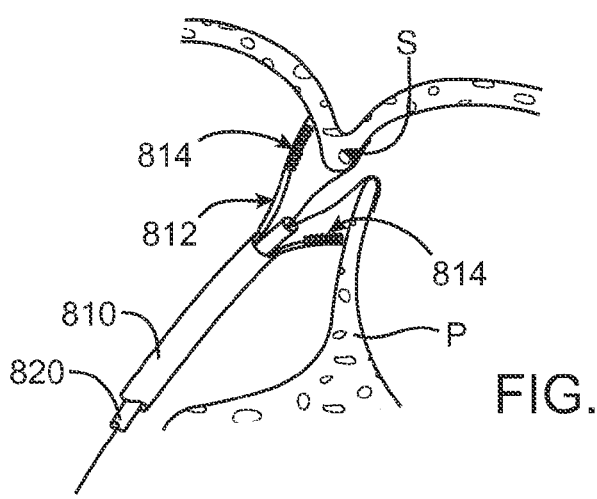
Figure 11D:
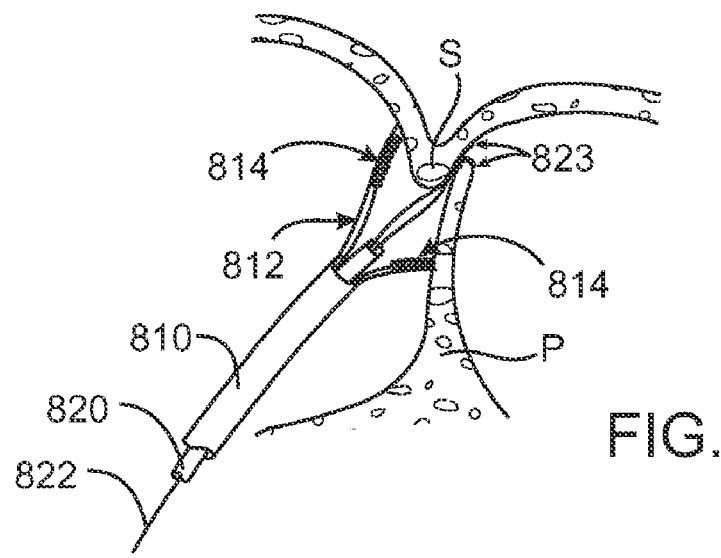
Figure 11E:
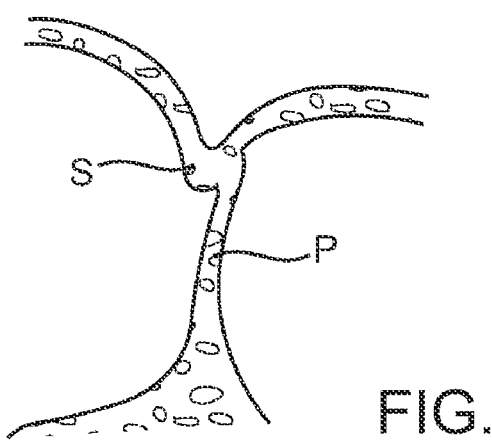

Once guide member 820 is in place and expandable member 822 is deployed, catheter device 810 may be advanced over guide member 820 to a position for treatment of the PFO as shown in FIG. 11C. Catheter device 810 typically includes a tissue apposition member 812 and one or more energy transmission members 814. Suction may be applied using tissue apposition member 812, left atrial pressure may be used, or both, to bring tissues P, S adjacent the PFO together, as shown in FIG. 11D. Once tissue apposition member 812 is placed and/or activated, guide member 820 and expandable member 822 may be removed through catheter device 810, leaving the tissues P, S apposed and catheter device in place, as in FIG. 11D. Alternatively, guide member 820 and expandable member 822 may be left in place during a first welding to close the majority of the PFO and then removed. The small patent portions of the PFO remaining after the guide member 820 and expandable member 822 are removed may then be closed by a second weld or may be left open and allowed to close via healing or scarring. Tissue apposition member 812 may be used to hold tissues P, S together before, during and/or after energy transmission members 814 weld the tissues T together. Such holding of the tissues together and application of energy to weld the tissues may be performed for any suitable time, such as for less than one second to many minutes. Once a sufficient amount of energy has been applied to the tissues P, S to acutely close the PFO, catheter device 810 is removed, leaving a closed PFO, as in FIG. 11E.

In FIG. 12A, the closure device 900 comprises an elongate flexible catheter shaft 902 disposed in an outer sheath 901, with the catheter shaft 902 having a wire-like radially expandable radiopaque basket 906 on its distal end. The wire-like basket 906 may include two or more flexible members that form the basket, or the basket may be formed from a braid or a helically wound wire form. The closure device 900 is advanced over a guide wire 904 into the PFO tunnel formed by tissue layers P and S. The basket 906 is typically biased in the expanded position such that the profile of the basket matches the size of a PFO tunnel. The proximal end of the guide wire 904 may be threaded into catheter shaft 902 and the distal end of catheter shaft 902 is attached to the basket 906. When catheter shaft 902 is advanced distally relative to outer sheath 901, the basket 906 becomes unconstrained as shown in FIG. 12B, and then basket 906 opens up such that it electrically contacts the tissues of the PFO. Once properly positioned, the wire-like basket 906 also acts as an electrode and allows energy to be delivered to the tissue defect. Energy may be delivered to the PFO tunnel while the closure device 900 remains stationary or as the device 900 is retracted, thus providing an "energy sweeping" method. As the PFO collapses, the basket 906 collapses as well.

Figure 16A:
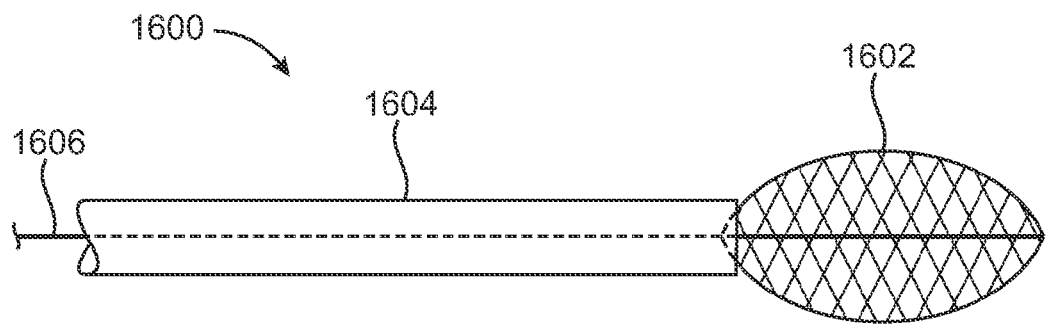
Figure 16B:
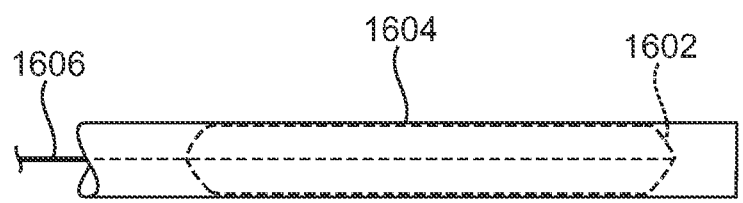

Other embodiments of wire-like or mesh baskets are shown in FIGS. 16A-18. In FIG. 16A, a mesh basket 1602 is disposed on the distal end of sheath 1604 in closure device 1600. The proximal and distal ends of the basket 1602 are preferably curved to facilitate entry into and exiting from a PFO tunnel. Additionally, the arcuate shape accommodates varying sizes of PFO tunnels. An axial member 1606 is slidably disposed along sheath 1604 and allows the basket 1602 to be advanced from the sheath 1604 or retracted into the sheath 1604. Axial member 1606 also provides electrical conductors from the proximal end of the closure device 1600 to the basket 1602. Portions of the basket 1602 are configured as energy transmission members and allow energy to be transferred between the basket 1602 and the tissues. In FIG. 16B, the axial member 1606 has been retracted proximally so as to retract basket 1602 back into sheath 1604 where it has a reduced profile.

Figure 17:
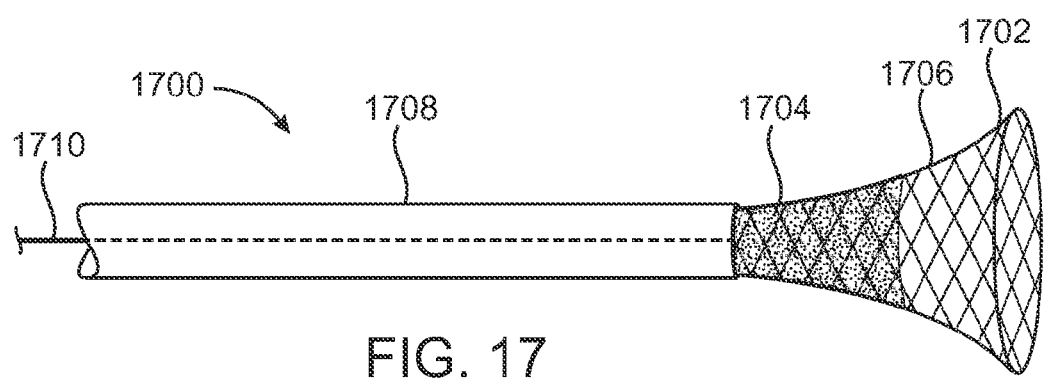

FIG. 17 shows another embodiment of a wire-like or mesh basket 1702. In FIG. 17, closure device 1700 comprises a shaped basket unconstrained at the distal end 1702 and disposed on the distal end of sheath 1708. The tapered shaped of the basket 1702 accommodates varying PFO tunnel sizes. Basket 1702 may be retracted into sheath 1708 in order to reduce the profile of closure device 1700, especially during delivery. Axial member 1710 is slidably disposed along sheath 1708 and is used to advance or retract basket 1702 to/from the sheath 1708. Additionally, axial member 1710 may also serve as an electrical conductor path between the wire basket and the proximal end of closure device 1700. A distal portion of the basket 1706 serves as an uninsulated energy transmission member, while a proximal portion of the basket 1704 is insulated to prevent energy delivery from this part of the basket. A thin conformal insulating coating is preferred so as to preserve the resilience of the device. Exemplary insulating materials include for example parylene.

Figure 18:
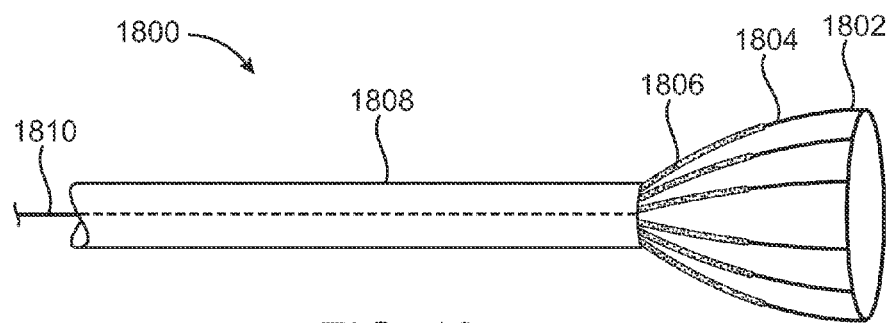

A conically shaped wire-like basket is shown in FIG. 18. In FIG. 18, a plurality of wires form a basket 1802 on the distal end of closure device 1800. An insulated region 1806 prevents energy transmission, while an uninsulated region 1804 is adapted to deliver energy to the tissue. An axial member 1810 allows the basket 1802 to be advanced from or retracted into sheath 1808 and also serves as an electrical conductor between the basket and the proximal end of closure device 1800.

Referring now to FIG. 13, in yet another embodiment, a catheter system 925 for treating PFO may include a first catheter body 926 having a first wire-like basket or expandable member 928, a second catheter body 936 having a second wire-like basket or expandable member 934 and a guide wire 930. The wire-like baskets 928, 934 generally take the same form as embodiments previously described herein, such as in FIGS. 12, 16A-16B, 17 or 18. In FIG. 13, both wire-like baskets 928, 934 are coaxial and in some embodiments the wire baskets 928, 934 may move independently of one another, while in other embodiments the wire baskets are fixed relative to one another. In one embodiment, guide wire 930 extends from an entry point on the patient, such as a femoral vein, through the inferior vena cava IVC, right atrium RA, PFO and left atrium LA, and then through the left ventricle, aorta, and eventually out a femoral artery. Catheter bodies 926, 936 may be advanced to locations in the right and left atria respectively along this guide wire. In an alternative embodiment, two guide wires may be used, and they may be coupled within the PFO or elsewhere within the heart. In either case, the wire-like baskets 928, 934 are advanced into the PFO tunnel until they are adjacent to one another. Energy may then be delivered from the wire-like baskets to the PFO tissue defect as both catheter bodies 926, 936 are retracted to the side of the PFO defect from which they were introduced. The guide wire 930 is withdrawn upon completion of the treatment. This method permits the PFO tunnel to be sealed from both sides of the heart.

Figure 14A:
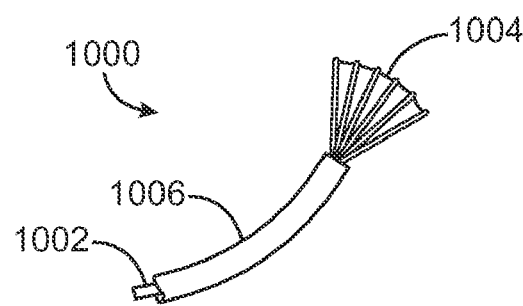
Figure 14B:
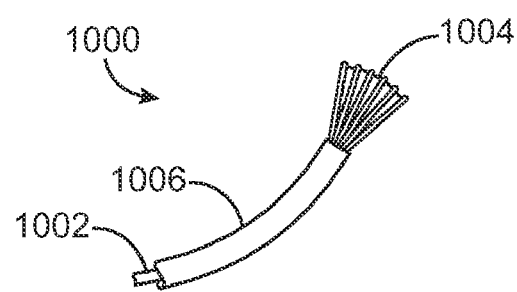
Figure 14C:
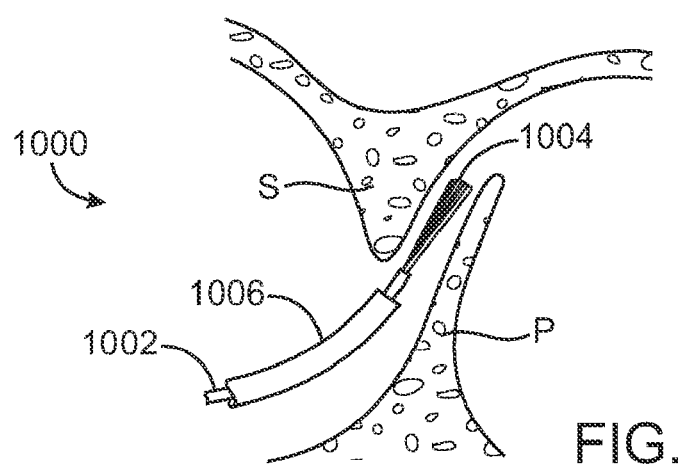
Figure 14D:
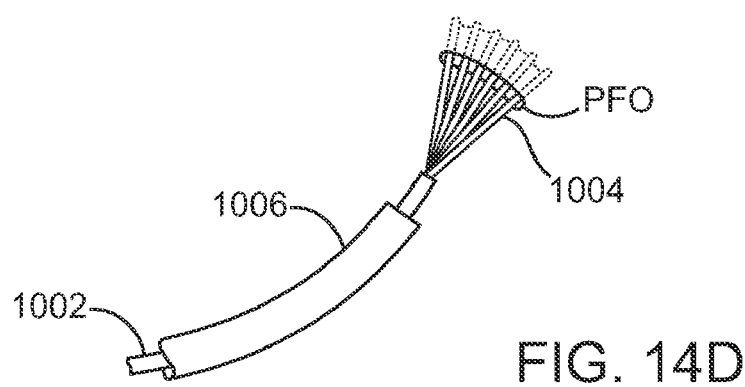

FIG. 14A shows still another embodiment of a closure treatment device 1000. In FIG. 14A, closure device 1000 comprises a catheter body 1002 having a retractable, flexible fan shaped energy transmission member 1004 on its distal end. An outer sheath 1006 is slidably disposed over the catheter body 1002 and may be advanced distally over the fan shaped energy transmission member 1004 to facilitate collapsing it and reducing its profile, as seen in FIG. 14B. The device 1000 is inserted in between layers of the tissue defect, P, S and the fan shaped energy transmission member 1004 is deployed from the catheter shaft 1002. The fan shaped energy transmission member is self-sizing and matches the tunnel diameter or tissue surfaces. FIGS. 14C and 14D show the fan shaped energy transmission member 1004 disposed in a PFO tunnel. As energy is delivered to the PFO tunnel, the tunnel closes around the energy transmission member 1004, which in turn collapses the fan shaped energy transmission member 1104 to a lower profile. The energy transmission member 1004 may then be retracted along the layered tissue defect, sealing the PFO as it is retracted. Alternatively, the fan shaped energy transmission member 1004 may be left in the tunnel and as the tunnel closes, the force of the collapsing tunnel causes the fan shaped member 1004 to collapse. Once the tunnel has collapsed and is substantially closed, the fan shaped member 1004 may then be retraced into the catheter body 1002 and removed form the PFO. Other fan shaped energy transmission members are disclosed in U.S. patent application Ser. No. 10/952,492, the contents of which have previously been incorporated by reference. In a variation on this embodiment, a self-sizing cone shaped energy transmission member 1104 is used in FIG. 15. The cone shaped member 1104 may similarly be retracted along the PFO tunnel as energy is applied to close the defect, or it may be left in the tunnel as the tunnel collapses and then retracted into the catheter body 1102 and removed from the tunnel.

In FIG. 20, closure device 2000 comprises a plurality of electrodes 2008 extending from the distal end of sheath 2002. Electrodes 2008 are disposed on elongated flexible beams and are used to deliver energy from the closure device to the tissue. Additionally, one or more thermocouples 2006 are also disposed on elongated flexible beams and the monitor tissue temperature. Tissue temperature is typically in the range from about 55° C. to about 150° C., often in the range from about 55° C. to about 90° C. and preferably in the range from about 65° C. to about 90° C. The electrodes 2008 as well as thermocouples 2006 may be withdrawn into the sheath 2002 when axial member 2004 is retracted proximally. Axial member 2004 also provides a conductive pathway from the electrodes 2008 and thermocouples 2006 to the proximal end of the closure device 2000.

In FIGS. 21A-21C, electrodes 2100 are formed from a flat sheet prior to attaching them to a closure device. In FIG. 21A, flat stock is cut to form a plurality of elongated resilient fingers 2104 attached to a base 2102. The flat stock may also be machined, laser cut, EDM machined or photochemically etched. In FIG. 21B, the flat sheet of electrodes 2100 is rolled and ends are joined together so as to form an electrode ring. Portions of the electrode resilient fingers 2104 may then be insulated 2108 while uninsulated regions 2106 permit energy transmission to or from the tissue. The resilient electrode fingers 2104 are typically insulated with a thin, conformal insulation which can be sprayed on or vapor deposition may also be employed. Examples of insulation include parylene, silicone or various other polymers. Once the electrodes have been formed, they are joined to the distal end of a closure device 2150 as shown in FIG. 21C. Typically the electrodes are connected to a catheter shaft 2152 which allows the electrodes to be advanced or retracted in the vascular system. A conductor 2154 allows energy to be supplied from the proximal end of catheter shaft 2152 to the electrode fingers 2104.

Other wire mesh or braided configurations are illustrated in FIGS. 22A-22C and FIG. 23. In FIG. 22A, the distal end of a closure device 2200 may comprise a wire-braid 2202 or mesh like tip having a cylindrical cross-section. The mesh structure could also include a coiled structure 2204 as shown in FIG. 22B or a helical structure 2206 illustrated in FIG. 22C. FIG. 23 shows how the cross-section of a closure device 2300 may easily be modified, here shown as a rectangular section 2302. In either case, the wire-braid or mesh structure may serve as an energy transmission member to transfer energy to or from the PFO during treatment. Various portions of the wire mesh may be insulated with a thin conformal coating such as parylene so that energy may be directed to specific portions of the wire mesh. Alternatively, the wire-mesh may remain uninsulated so that energy is delivered along the entire length of the wire mesh. Portions of the energy transmission member may also be formed such as a laterally extending electrode as described in U.S. patent application Ser. No. 10/952,492 the entire contents of which are incorporated herein by reference.

Additionally, the shape of the wire mesh may easily be adjusted as shown in FIGS. 24A-24B. In FIG. 24A, a close device 2400 comprises a wire braid distal tip 2402 having a short cylindrical profile. The proximal end of the wire braid 2410 is coupled to an inner shaft 2408 and a rigid wire 2406 is coupled with the distal end of the wire mesh 2404. The entire assembly is deployable from a sheath 2412. By pushing or pulling rigid wire 2406, the shape of the wire mesh may be adjusted as seen in FIG. 24B. In FIG. 24B, wire 2406 has been pushed distally, elongating the wire mesh and reducing its diameter into a longer, smaller diameter cylinder 2403 as compared with its original shape 2402. Additionally, by adjusting the wire mesh geometry, it may be adjusted to provide a lateral force to the PFO which would help bring the tissues into apposition with an electrode or other energy transmission member. Other embodiments described herein may similarly be used.

Figure 25A:
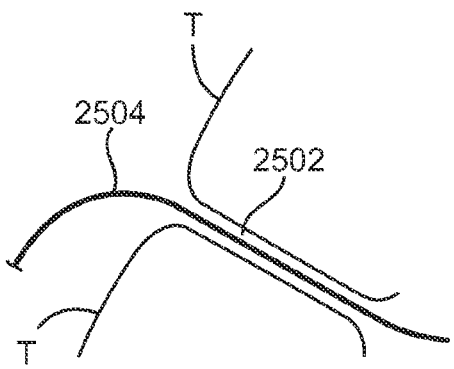
Figure 25B:
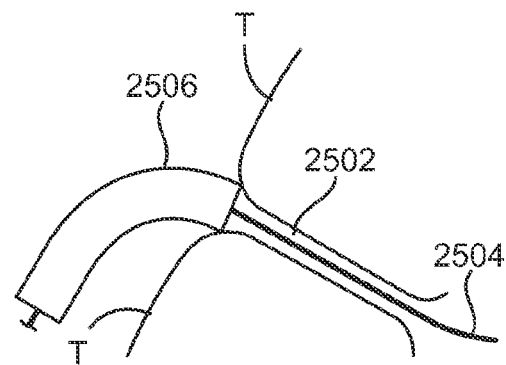
Figure 25C:
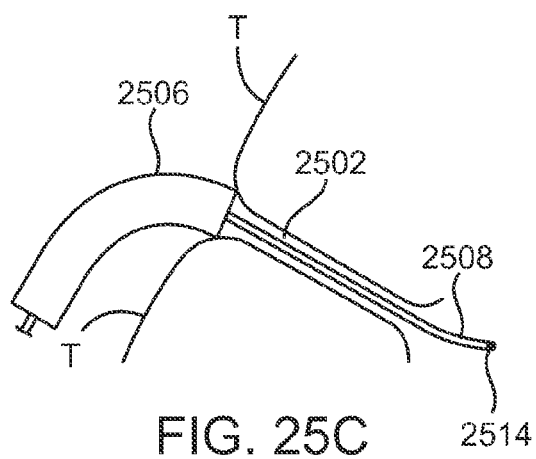

FIGS. 25A-25F illustrate a method of treating a layered tissue defect such as a PFO in accordance with another embodiment of the present invention. In FIG. 25A, a guide wire 2504 is advanced through the patient's vasculature into the right side of a patient's heart. The guide wire 2504 is advanced between tissue layers T forming the PFO tunnel 2502. Guide wire 2504 position may be monitored under fluoroscopy or using intracardiac ultrasound. In some embodiments, the guide wire 2504 is also an electrode which can then deliver energy to the tissue to close the PFO, and this has been discussed with respect to FIGS. 8A-8D above. In this embodiment, once the guide wire 2504 has been successfully placed in the PFO, it acts as a guide rail as shown in FIG. 25B where catheter 2506 is advanced over the guide wire 2504 until it is in apposition with tissues T of the PFO. An energy transmission wire 2508 similar to the embodiment of FIG. 8A is then advanced through the catheter 2506 into the PFO tunnel 2502 and the original guide wire 2504 is removed, as illustrated in FIG. 25C. The energy transmission wire 2508 is insulated along its length except for a region approximately 0.5 cm to 1 cm away from the distal end of the energy transmission wire 2508. The energy transmission wire 2508 is inserted into the tunnel 2502 such that the uninsulated region is adjacent to the PFO tunnel exit closest to the left side of the heart, although in some embodiments, the energy transmission wire 2508 could be inserted so that it is co-terminus with the PFO tunnel exit.

Figure 25D:
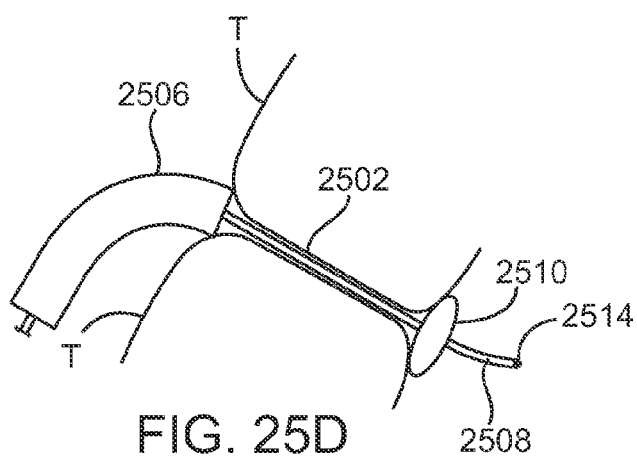
Figure 25E:
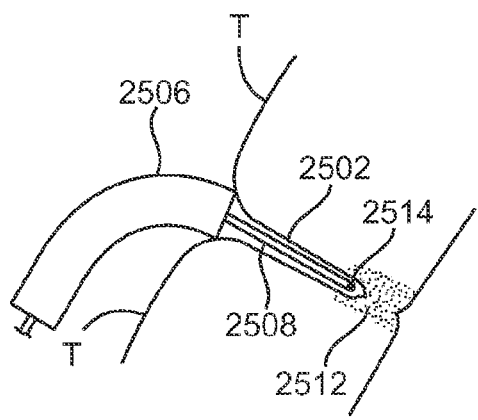
Figure 25F:
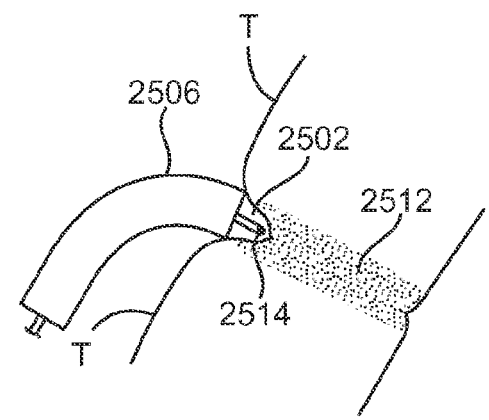

In FIG. 25D, catheter 2506 applies a vacuum to the tissues T of the PFO in order to draw the tissues T toward the energy transmission wire 2508. Optionally, a backstop element 2510 may be placed on the left side of the PFO tunnel in order to block the exit and help the suction collapse the tunnel 2502. In FIG. 25E, while vacuum is applied by catheter 2506 to the tissues T of the PFO, monopolar radiofrequency energy is delivered from the energy transmission wire 2508 to the tissues T of the PFO. The radiofrequency energy generates heat which in turn collapses and fuses the tissues T of the tunnel together 2512. Simultaneously, the energy transmission member 2508 is retracted proximally out of the tunnel 2502, and thus the tunnel becomes sealed along its length 2512 as seen in FIG. 25F. A temperature monitoring device such as a thermistor or thermocouple 2514 may be placed on the energy transmission wire 2508 to allow monitoring of the treatment. After the PFO tunnel has been sealed, the wire and catheter may be removed from the patient.

Additionally, as mentioned above, the method described herein may be altered in any number of ways without departing from the scope of the invention. In some embodiments, for example, tissues adjacent the PFO are brought at least partially together and energy is applied to the tissues to acutely close the PFO with fewer steps and/or fewer device components than described. For example, application of suction to appose tissues is not required in all embodiments. Furthermore, a variety of different types of energy may be applied to the tissues from a variety of differently configured energy transmission devices. In some embodiments, one or more of the steps described above may be repeated one or more times, such as by repeating a tissue welding step. In still other embodiments, energy transmission members may be swept along the tissues of the defect to cause a closure in the defect, or they also may be placed in the PFO tunnel and retracted during energy delivery and sealing of the tunnel. The above description, therefore, is provided for exemplary purposes only.

Although the foregoing description is complete and accurate, it has described only exemplary embodiments of the invention. Various changes, additions, deletions and the like may be made to one or more embodiments of the invention without departing from the scope of the invention. Additionally, different elements of the invention could be combined to achieve any of the effects described above. Thus, the description above is provided for exemplary purposes only and should not be interpreted to limit the scope of the invention as set forth in the following claims.

What is claimed is:

1. A method for closing a layered tissue defect, the method comprising:
   inserting a first closure device into the layered tissue defect, the first closure device including two conductive elements, the two conductive elements each including an insulated proximal portion, a positive stop, and an uninsulated distal energy transmission portion;
   positioning the first closure device without penetrating the layers of the tissues so that the positive stops of the two conductive elements engage peripheral limits of the layered tissue defect in order to allow passage of the closure device to a predetermined depth within the layered tissue defect;

applying energy to the layered tissue defect with the first closure device at a first position;

applying energy to the layered tissue defect at a second position adjacent to the first position so as to substantially close the layered tissue defect along at least a portion of the defect; and removing the first closure device from the layered tissue defect.

2. A method as in claim 1, wherein the layered tissue defect is a patent foramen ovale.

3. A method as in claim 1, wherein the first closure device comprises an electrode.

4. A method as in claim 1, wherein energizing the first closure device comprises delivering monopolar energy.

5. a method as in claim 1, wherein energizing the first closure device comprises delivering bipolar energy.

6. A method as in claim 1, wherein energizing the first closure device comprises delivering one of radiofrequency energy, cryogenic energy, resistive heat energy, heat energy, ultrasound energy, microwave energy and laser energy.

7. A method as in claim 1, further comprising delivering a cross-linking agent to the layered tissue defect.

8. A method as in claim 1, wherein the layered tissue defect is a patent foramen ovale having a tunnel, the tunnel having a right atrial opening, and a left atrial opening, and further wherein the first position is at a location within the layered tissue defect that is closer to the left atrial opening, and the second position is at a location within the layered tissue defect that is closer to the right atrial opening.

9. A method as in claim 1, wherein removing the first closure device comprises retracting the first closure device into an elongate flexible member.

10. A method as in claim 1, wherein removing the first closure device comprises retracting the first closure device as the closure device collapses to a reduced profile.

11. A method as in claim 1, wherein applying energy at the first position and the second position substantially closes a distal portion of the defect.

12. A method for closing a layered tissue defect, the method comprising:

inserting a first closure device into the layered tissue defect, the first closure device including two conductive elements, the two conductive elements each including an insulated proximal portion, a positive stop, and an uninsulated distal energy transmission portion;

positioning the first closure device without penetrating the layers of the tissues so that the positive stops of the two conductive elements engage peripheral limits of the layered tissue defect in order to allow passage of the closure device to a predetermined depth within the layered tissue defect;

applying energy to the layered tissue defect with the first closure device while withdrawing the first closure device from the layered tissue defect.

13. A method as in claim 12, wherein the layered tissue defect is a patent foramen ovale.

14. A method as in claim 12, wherein the first closure device comprises an electrode.

15. A method as in claim 12, wherein energizing the first closure device comprises delivering monopolar energy.

16. A method as in claim 12, wherein energizing the first closure device comprises delivering bipolar energy.

17. A method as in claim 12, wherein energizing the first closure device comprises delivering one of radiofrequency energy, cryogenic energy, resistive heat energy, heat energy, ultrasound energy, microwave energy and laser energy.

18. A method as in claim 12, further comprising delivering a cross-linking agent to the layered tissue defect.

19. A method as in claim 12, wherein the layered tissue defect is a patent foramen ovale having a tunnel, the tunnel having a right atrial opening, and a left atrial opening, and further wherein the first position is at a location within the layered tissue defect that is closer to the left atrial opening, and the second position is at a location within the layered tissue defect that is closer to the right atrial opening.

20. A method as in claim 12, wherein removing the first closure device comprises retracting the first closure device into an elongate flexible member.

21. A method as in claim 12, wherein removing the first closure device comprises retracting the first closure device as the first closure device collapses to a reduced profile.

* * * * *